(12) United States Patent
MacDonald et al.

(10) Patent No.: US 9,040,707 B2
(45) Date of Patent: May 26, 2015

(54) BICYCLIC THIAZOLES AS ALLOSTERIC MODULATORS OF MGLUR5 RECEPTORS

(75) Inventors: Gregor James MacDonald, Zoersel (BE); Andrés Avelino Trabanco-Suárez, Olias del Rey (Toledo) (ES); Susana Conde-Ceide, Toledo (ES); Gary John Tresadern, Toledo (ES); José Manuel Bartolomé-Nebreda, Toledo (ES); Joaquin Pastor-Fernández, Toledo (ES)

(73) Assignee: Janssen Pharmaceutica NV, Beerse (BE)

( * ) Notice: Subject to any disclaimer, the term of this patent is extended or adjusted under 35 U.S.C. 154(b) by 52 days.

(21) Appl. No.: 13/516,985

(22) PCT Filed: Dec. 16, 2010

(86) PCT No.: PCT/EP2010/069957
§ 371 (c)(1),
(2), (4) Date: Jun. 18, 2012

(87) PCT Pub. No.: WO2011/073339
PCT Pub. Date: Jun. 23, 2011

(65) Prior Publication Data
US 2012/0258955 A1      Oct. 11, 2012

(30) Foreign Application Priority Data

Dec. 18, 2009  (EP) .................................. 09179850
Nov. 29, 2010  (EP) .................................. 10193019

(51) Int. Cl.
*A61K 31/4365*    (2006.01)
*C07D 513/04*     (2006.01)

(52) U.S. Cl.
CPC .......... *C07D 513/04* (2013.01); *A61K 31/4365* (2013.01)

(58) Field of Classification Search
CPC ......................... C07D 513/04; A61K 31/4365
USPC .......................................... 546/114; 514/301
See application file for complete search history.

(56) References Cited

U.S. PATENT DOCUMENTS

| | | | |
|---|---|---|---|
| 5,753,664 | A | 5/1998 | Aono et al. |
| 7,893,069 | B2 | 2/2011 | Kuehnert et al. |
| 8,242,116 | B2 | 8/2012 | Alexander et al. |
| 2009/0163545 | A1 | 6/2009 | Goldfarb |
| 2010/0081690 | A1 | 4/2010 | LePoul et al. |
| 2013/0029904 | A1 | 1/2013 | Kukolj |

FOREIGN PATENT DOCUMENTS

| | | |
|---|---|---|
| WO | WO 2004/038374 | 5/2004 |
| WO | 2005/082856 | 9/2005 |
| WO | 2006/066174 | 6/2006 |
| WO | 2006/074884 | 7/2006 |
| WO | WO 2007/007040 | 1/2007 |
| WO | 2007/023290 | 3/2007 |
| WO | WO 2007/023242 | 3/2007 |
| WO | 2007/056366 | 5/2007 |
| WO | 2007/104485 | 9/2007 |
| WO | 2008/001076 | 1/2008 |
| WO | WO 2008/012010 | 1/2008 |
| WO | 2008/060597 | 5/2008 |
| WO | WO 2008/060597 | 5/2008 |
| WO | 2008/066174 | 6/2008 |
| WO | 2008/076562 | 6/2008 |
| WO | 2008/151184 | 12/2008 |
| WO | 2010/114971 | 10/2010 |
| WO | 2011/072370 | 6/2011 |
| WO | 2011/073339 | 6/2011 |

OTHER PUBLICATIONS

International Search Report for PCT/EP2010/069957 dated Apr. 4, 2011.
Database Beilstein, (Jan. 2010) XP002580527, No. BRN977498, Lehmann G.et al.
Stepanov et al., 2002, Database Caplus XP 002580528, Accession nr. 2002:250236, RN 441771-46-6, RN 312526-80-0.
Billingsley, et al., J. Org. Chem. 2008, 73(14), 5589-5591.
Chinchilla et al., Chem. Rev. 2007, 107(3), 874-922.
Chrovian et al., Org. Lett. 2008, 10(5), 811-814.
Collison et al., Synthesis, 2006, 14, 2319-2322.
Kew and Kemp Psychopharmacol., 2005, 179:4-29.
Mutel, Expert Opin. Ther. Patents, 2002, 12:1-8.
Orita et al., Chem. Rev. 2006, 106(12), 5387-5412.
Roppe et al.; Bioorganic & Medicinal Chem.14, 3993-3996 (2004).
Schoepp D. D. et al. Neuropharmacology, 1999, 38(10), 1431-1476.
Takagi et al., J. Am. Chem. Soc. 2002, 124(27), 8001-8006.
Valgeirsson et al.; Bioorganic & Medicinal Chem.11, 4341-4349 (2003).
Cozzoli et al., J Neurosci. Jul. 8, 2009; 29(27): 8655-8668.
Liu et al., Journal of Neurochemistry, 2005, 95, 1363-1372.

*Primary Examiner* — David K O Dell
(74) *Attorney, Agent, or Firm* — Hal B. Woodrow

(57) ABSTRACT

The present invention relates to novel bicyclic thiazoles which are positive allosteric modulators of the metabotropic glutamate receptor subtype 5 ("mGluR5") and which are useful for the treatment or prevention of disorders associated with glutamate dysfunction and diseases in which the mGluR5 subtype of receptors is involved. The invention is also directed to pharmaceutical compositions comprising such compounds, to processes for preparing such compounds and compositions, and to the use of such compounds and compositions for the prevention and treatment of disorders in which mGluR5 is involved.

7 Claims, 1 Drawing Sheet

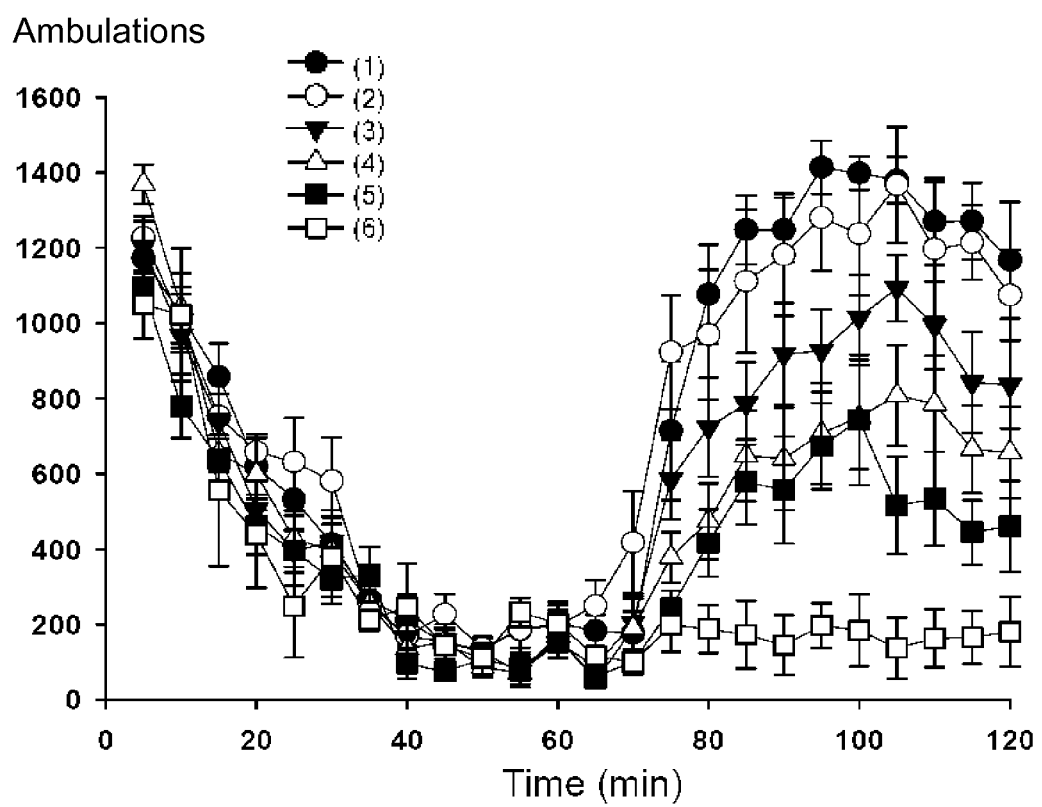

BICYCLIC THIAZOLES AS ALLOSTERIC MODULATORS OF MGLUR5 RECEPTORS

CROSS REFERENCE TO RELATED APPLICATIONS

This application is the national stage of PCT Application No. PCT/EP2010/069957, filed Dec. 16, 2010, which claims priority from European Patent Application No. 09179850.4, filed Dec. 18, 2009, and European Patent Application No. 10193019.6, filed Nov. 29, 2010, the entire disclosures of which are hereby incorporated in their entirety.

FIELD OF THE INVENTION

The present invention relates to novel bicyclic thiazoles which are positive allosteric modulators of the metabotropic glutamate receptor subtype 5 ("mGluR5") and which are useful for the treatment or prevention of disorders associated with glutamate dysfunction and diseases in which the mGluR5 subtype of receptors are involved. The invention is also directed to pharmaceutical compositions comprising such compounds, to processes for preparing such compounds and compositions, and to the use of such compounds and compositions for the prevention and treatment of disorders in which mGluR5 is involved.

BACKGROUND OF THE INVENTION

Glutamate is the major amino acid neurotransmitter in the mammalian central nervous system. Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptors channels (iGluRs), and the NMDA, AMPA and kainate receptors which are responsible for fast excitatory transmission (Kew and Kemp Psychopharmacol., (2005), 179:4-29).

In addition, glutamate activates metabotropic glutamate receptors (mGluRs) which have a more modulatory role that contributes to the fine-tuning of synaptic efficacy.

Glutamate activates the mGluRs through binding to the large extracellular amino-terminal domain of the receptor, herein called the orthosteric binding site. This binding induces a conformational change in the receptor which results in the activation of the G-protein and intracellular signaling pathways.

mGluR5 and NMDA receptors are co-expressed in hippocampus, cortex and striatum.

mGluR5 potentiates NMDA receptor function via a PKC- and Src-dependent mechanism. Blockade of mGluR5 or NMDA receptors impairs cognitive function whereas activation of mGluR5 or NMDA receptors normalizes amphetamine disrupted pre-pulse inhibition (PPI). Stimulation of mGluR5 receptors is postulated to normalize the NMDA receptor hypofunction in schizophrenia. An mGluR5 positive allosteric modulator (PAM) may have beneficial effects on cognition, positive and negative symptoms of schizophrenia, and cognitive deficits in various forms of dementia and mild cognitive impairment.

To date, most of the available pharmacological tools targeting mGluRs are orthosteric ligands which cross react with several members of the family as they are structural analogues of glutamate and have limited bioavailability (Schoepp D. D. et al. Neuropharmacology (1999), 38(10), 1431-1476). A new avenue for developing selective compounds acting at mGluRs is to identify molecules that act through allosteric mechanisms, modulating the receptor by binding to a site different from the highly conserved glutamate binding site. Positive allosteric modulators of mGluRs have emerged recently as novel pharmacological entities offering this attractive alternative. This type of molecule has been discovered for several mGluR sub-types (reviewed in Mutel (2002) Expert Opin. Ther. Patents 12:1-8).

WO-2005/082856, WO-2007/023242 and WO-2007/023290 (Merz) disclose tetrahydroquinolinones as modulators of Group I mGluRs. WO 2008/151184 (Vanderbilt University) discloses benzamides as mGluR5 positive allosteric modulators. Fused thiazole compounds are further known from amongst others WO-2008/060597 (Vertex), WO-2008/076562 (Lilly), WO-2008/001076 (UCB), WO-2008/066174 (Lilly) and WO-2006/066174 (Eli Lilly). US 2010/0081690 (Addex Pharma, S.A.) published on Apr. 1, 2010 discloses oxazole derivatives as positive allosteric modulators of mGluR5. WO 2008/012010 (UCB Pharma, S.A.) published on Jan. 31, 2008 discloses fused oxazoles and thiazoles as Histamine H3-receptor ligands with groups at the 2-position of the thiazole ring that are different to the ones disclosed herein. WO 2010/114971 (Sepracor Inc.), published on Oct. 7, 2010 discloses bicyclic compounds and provides data for their activity as mGluR5 NAMs; none of the compounds disclosed therein contain a substituent at the 2-position of the thiazole ring as disclosed herein, and none of the exemplified compounds contain a carbonyl group in the bicyclic core.

It is the object of the present invention to provide novel compounds with an improved balance of properties over the prior compounds, in particular, advantageous properties such as central penetration, improved in vivo potency at lower dose and/or improved pharmacokinetic properties.

DESCRIPTION OF THE INVENTION

The present invention relates to compounds having metabotropic glutamate receptor 5 modulator activity, said compounds having the Formula (I)

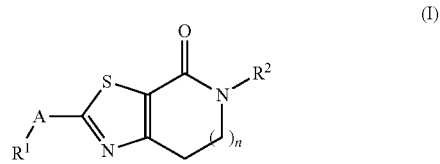

and the stereoisomeric forms thereof,
wherein
n is 1 or 2;
A is selected from the group consisting of —CH$_2$O— and —O—CH$_2$—;
R$^1$ is selected from the group consisting of phenyl and phenyl substituted with 1, 2 or 3 substituents each independently selected from the group consisting of C$_{1-6}$alkyl, trifluoromethyl, cyano and halo; and
R$^2$ is selected from the group consisting of hydrogen; C$_{1-8}$alkyl; (C$_{1-6}$alkyloxy)C$_{1-3}$alkyl; C$_{3-8}$cycloalkyl; (C$_{3-8}$cycloalkyl)C$_{1-3}$alkyl; phenyl; phenyl substituted with 1, 2 or 3 substituents each independently selected from the group consisting of C$_{1-6}$alkyl, C$_{1-3}$alkyloxy, halo and C$_{1-3}$alkyl substituted with 1, 2 or 3 independently selected halo substituents; (phenyl)$C_{1-3}$alkyl; (phenyl)$C_{1-3}$alkyl wherein the phenyl part is substituted with 1, 2 or 3 independently selected halo substituents; pyridinyl; pyridinyl substituted with 1 or 2 substituents each independently selected from the group consisting of $C_{1-6}$alkyl, $C_{1-3}$alkyloxy, halo and $C_{1-3}$alkyl substituted with 1, 2 or 3 independently selected halo substituents; and (tetrahydro-2H-pyranyl)-methyl; and the pharmaceutically acceptable salts and the solvates thereof.

The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament and to a compound of Formula (I) for use as a medicament for the treatment or prevention of neurological and psychiatric disorders in which mGluR5 is involved.

The invention also relates to the use of a compound according to Formula (I) or a pharmaceutical composition according to the invention for the manufacture of a medicament for treating or preventing neurological and psychiatric disorders in which mGluR5 is involved.

Additionally, the invention relates to the use of a compound of Formula (I) in combination with an additional pharmaceutical agent for the manufacture of a medicament for treating or preventing neurological and psychiatric disorders in which mGluR5 is involved.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a product comprising a compound of Formula (I) and an additional pharmaceutical agent, as a combined preparation for simultaneous, separate or sequential use in the prevention, treatment or prophylaxis of neurological and psychiatric disorders and diseases.

The chemical names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006). In case of tautomeric forms, the name of the depicted tautomeric form of the structure was generated. However, it should be clear that the other non-depicted tautomeric form is also included within the scope of the present invention.

For the avoidance of doubt, A corresponds to a bivalent linker of formula —$CH_2$—O—, —O—$CH_2$—, wherein the definition is to be read from left to right, going from the bicyclic core of the molecule to $R^1$. Thus, when A is —$CH_2$—O—, the —$CH_2$— is bound to the bicycle and —O— is attached to $R^1$; when A is —O—$CH_2$—, the —O— is bound to the bicycle and the —$CH_2$— is bound $R^1$.

BRIEF DESCRIPTION OF DRAWINGS

FIG. 1 graphically presents the data from the dose-dependent reversal effects of compound 8 on amphetamine-induced hyperlocomotion described in the Pharmacological Examples.

In the FIGURE, (1)-(6) have the following meaning:
(1) 20% 2-hydroxypropyl-β-cyclodextrin p.o. (oral gavage administration)/Amphetamine sulphate 1.0 kg/mg s.c. (administered subcutaneously).
(2) Compound 8 (3.0 mg/kg p.o.)/Amphetamine sulphate (1.0 mg/kg s.c.)
(3) Compound 8 (10.0 mg/kg p.o.)/Amphetamine sulphate (1.0 mg/kg s.c.)
(4) Compound 8 (30.0 mg/kg p.o.)/Amphetamine sulphate (1.0 mg/kg s.c.)
(5) Compound 8 (56.6 mg/kg p.o.)/Amphetamine sulphate (1.0 mg/kg s.c.)
(6) Vehicle (pH 7) p.o./Vehicle (pH 7) s.c.
The vehicle for compound 8 is 20% wt/v 2-hydroxypropyl-β-cyclodextrin and the vehicle for amphetamine is sterile water. "Ambulations" corresponds to the "Total Beam Breaks/5 minute intervals".

DETAILED DESCRIPTION OF THE INVENTION

Definitions

The term "halogen" or "halo" as used herein alone or as part of another group refers to fluorine, chlorine, bromine or iodine, with fluorine or chlorine being preferred, and fluoro being particularly preferred.

The term "$C_{1-3}$alkyl", "$C_{1-6}$alkyl" or "$C_{1-8}$alkyl" as employed herein alone or as part of another group, unless otherwise stated, refers to a saturated straight or branched, optionally substituted hydrocarbon chain radical, having from 1 to 3 or from 1 to 6 or from 1 to 8 carbon atoms unless otherwise stated, which is attached to the rest of the molecule by a single bond, which includes but is not limited to methyl, ethyl, 1-propyl, 1-butyl, 1-pentyl, 1-methylethyl, 1,1-dimethylethyl, 2-methylpropyl, 3-methylbutyl, 1,2-dimethylpropyl, 1-hexyl, 1,2,2-trimethylpropyl, 1-ethyl-2,2-dimethylpropyl, 1,1,2,2-tetramethylpropyl, 1-heptyl and 1-octyl.

The term "$C_{3-8}$cycloalkyl" as employed herein alone or as part of another group unless otherwise stated, is generic to cyclopropyl, cyclobutyl, cyclopentyl, cyclohexyl, cycloheptyl and cyclooctyl.

The term "$C_{1-3}$alkyl substituted with 1, 2 or 3 independently selected halo substituents" as employed herein is generic to an alkyl group as defined above, substituted with 1, 2 or 3 halogen atoms at any available position, such as for example fluoromethyl; difluoromethyl; trifluoromethyl; 2,2,2-trifluoroethyl; 1,1-difluoroethyl; 3,3,3-trifluoropropyl. Preferred examples of these groups are trifluoromethyl; 2,2,2-trifluoroethyl and 1,1-difluoroethyl, with trifluoromethyl being particularly preferred.

In a particular embodiment, the invention relates to compounds of Formula (I), wherein
n is 1 or 2;
A is selected from the group consisting of —$CH_2$O— and —O—$CH_2$—;
$R^1$ is selected from the group consisting of phenyl; phenyl substituted with 1, 2 or 3 substituents each independently selected from the group consisting of $C_{1-6}$alkyl and fluoro; and 3-cyanophenyl; and
$R^2$ is selected from the group consisting of hydrogen; $C_{1-6}$alkyl; ($C_{1-6}$alkyloxy)$C_{1-3}$alkyl; $C_{3-8}$cycloalkyl; ($C_{3-8}$cycloalkyl)$C_{1-3}$alkyl; phenyl; phenyl substituted with 1, 2 or 3 substituents each independently selected from the group consisting of $C_{1-3}$alkyl, $C_{1-3}$alkyloxy, halo and $C_{1-3}$alkyl substituted with 1, 2 or 3 independently selected halo substituents; (phenyl)$C_{1-3}$alkyl; (phenyl)$C_{1-3}$alkyl wherein the phenyl part is substituted with 1, 2 or 3 independently selected halo substituents; pyridinyl; pyridinyl substituted with 1 or 2 substituents each independently selected from the group consisting of $C_{1-3}$alkyl, $C_{1-3}$alkyloxy, halo and $C_{1-3}$alkyl substituted with 1, 2 or 3 independently selected halo substituents; and (tetrahydro-2H-pyranyl)-methyl;

and the pharmaceutically acceptable salts and the solvates thereof.

In a particular embodiment, the invention relates to compounds of Formula (I), wherein n is 1 or 2;

A is selected from the group consisting of —CH$_2$O— and —O—CH$_2$—;

R$^1$ is selected from the group consisting of phenyl; phenyl substituted with 1, 2 or 3 substituents each independently selected from the group consisting of C$_{1-3}$alkyl and fluoro; and 3-cyanophenyl; and R$^2$ is selected from the group consisting of hydrogen; C$_{1-6}$alkyl; (C$_{1-6}$alkyloxy)C$_{1-3}$alkyl; C$_{3-8}$cycloalkyl; (C$_{3-8}$cycloalkyl)C$_{1-3}$alkyl; phenyl; phenyl substituted with 1, 2 or 3 substituents each independently selected from the group consisting of C$_{1-3}$alkyl, C$_{1-3}$alkyloxy, halo and C$_{1-3}$alkyl substituted with 1, 2 or 3 independently selected halo substituents; (phenyl)C$_{1-3}$alkyl; (phenyl)C$_{1-3}$alkyl wherein the phenyl part is substituted with 1, 2 or 3 independently selected halo substituents; pyridinyl; pyridinyl substituted with 1 or 2 substituents each independently selected from the group consisting of C$_{1-3}$alkyl, C$_{1-3}$alkyloxy, halo and C$_{1-3}$alkyl substituted with 1, 2 or 3 independently selected halo substituents; and (tetrahydro-2H-pyranyl)-methyl;

and the pharmaceutically acceptable salts and the solvates thereof.

In an embodiment, R$^2$ is selected from the group consisting of C$_{1-6}$alkyl; (C$_{1-6}$alkyloxy)C$_{1-3}$alkyl; (C$_{3-8}$cycloalkyl)C$_{1-3}$alkyl; phenyl; phenyl substituted with 1, 2 or 3 substituents each independently selected from the group consisting of C$_{1-3}$alkyl, C$_{1-3}$alkyloxy, halo and C$_{1-3}$alkyl substituted with 1, 2 or 3 independently selected halo substituents; (phenyl)C$_{1-3}$alkyl; (phenyl)C$_{1-3}$alkyl wherein the phenyl part is substituted with 1, 2 or 3 independently selected halo substituents; pyridinyl; pyridinyl substituted with 1 or 2 substituents each independently selected from the group consisting of C$_{1-3}$alkyl, C$_{1-3}$alkyloxy, halo and C$_{1-3}$alkyl substituted with 1, 2 or 3 independently selected halo substituents; and (tetrahydro-2H-pyranyl)-methyl; and n, A and R$^1$ are as previously defined.

In a particular embodiment, the invention relates to compounds of Formula (I), wherein n is 1 or 2;

A is —CH$_2$O—;

R$^1$ is selected from the group consisting of phenyl and phenyl substituted with 1, 2 or 3 substituents each independently selected from the group consisting of C$_{1-3}$alkyl and fluoro; and 3-cyanophenyl; and R$^2$ is selected from the group consisting of hydrogen; methyl; ethyl; 1,2,2-trimethyl-propyl; (C$_{1-6}$alkyloxy)C$_{1-3}$alkyl; C$_{3-8}$cycloalkyl; (C$_{3-8}$cycloalkyl)C$_{1-3}$alkyl; phenyl; phenyl substituted with 1, 2 or 3 substituents each independently selected from the group consisting of C$_{1-3}$alkyl, C$_{1-3}$alkyloxy, halo and C$_{1-3}$alkyl substituted with 1, 2 or 3 independently selected halo substituents; (phenyl)C$_{1-3}$alkyl; (phenyl)C$_{1-3}$alkyl wherein the phenyl part is substituted with 1, 2 or 3 independently selected halo substituents; pyridinyl; pyridinyl substituted with 1 or 2 substituents each independently selected from the group consisting of C$_{1-3}$alkyl, C$_{1-3}$alkyloxy, halo and C$_{1-3}$alkyl substituted with 1, 2 or 3 independently selected halo substituents; and (tetrahydro-2H-pyranyl)-methyl;

and the pharmaceutically acceptable salts and the solvates thereof.

In an embodiment, R$^2$ is selected from the group consisting of hydrogen; methyl; ethyl; 1,2,2-trimethyl-propyl; (C$_{1-6}$alkyloxy)C$_{1-3}$alkyl; (C$_{3-8}$cycloalkyl)C$_{1-3}$alkyl; phenyl; phenyl substituted with 1, 2 or 3 substituents each independently selected from the group consisting of C$_{1-3}$alkyl, C$_{1-3}$alkyloxy, halo and C$_{1-3}$alkyl substituted with 1, 2 or 3 independently selected halo substituents; (phenyl)C$_{1-3}$alkyl; (phenyl)C$_{1-3}$alkyl wherein the phenyl part is substituted with 1, 2 or 3 independently selected halo substituents; pyridinyl; pyridinyl substituted with 1 or 2 substituents each independently selected from the group consisting of C$_{1-3}$alkyl, C$_{1-3}$alkyloxy, halo and C$_{1-3}$alkyl substituted with 1, 2 or 3 independently selected halo substituents; and (tetrahydro-2H-pyranyl)-methyl; and n, A and R$^1$ are as previously defined.

In a particular embodiment, the invention relates to compounds of Formula (I), wherein n is 1 or 2;

A is —CH$_2$O—;

R$^1$ is selected from the group consisting of phenyl and phenyl substituted with 1 or 2 substituents each independently selected from the group consisting of C$_{1-3}$alkyl and fluoro; and R$^2$ is selected from the group consisting of hydrogen; methyl; ethyl; 1,2,2-trimethyl-propyl; (C$_{1-6}$alkyloxy)C$_{1-3}$alkyl; (C$_{3-8}$cycloalkyl)C$_{1-3}$alkyl; phenyl; phenyl substituted with 1 or 2 substituents each independently selected from the group consisting of C$_{1-3}$alkyl, C$_{1-3}$alkyloxy, halo and C$_{1-3}$alkyl substituted with 1, 2 or 3 independently selected halo substituents; (phenyl)C$_{1-3}$alkyl; (phenyl)C$_{1-3}$alkyl wherein the phenyl part is substituted with 1 or 2 independently selected halo substituents; pyridinyl; pyridinyl substituted with 1 or 2 substituents each independently selected from the group consisting of C$_{1-3}$alkyl, C$_{1-3}$alkyloxy, halo and C$_{1-3}$alkyl substituted with 1, 2 or 3 independently selected halo substituents; and (tetrahydro-2H-pyranyl)-methyl;

and the pharmaceutically acceptable salts and the solvates thereof.

In a particular embodiment, the invention relates to compounds of Formula (I), wherein n is 1 or 2;

A is —CH$_2$O—;

R$^1$ is selected from the group consisting of phenyl and phenyl substituted with 1 or 2 substituents each independently selected from the group consisting of C$_{1-3}$alkyl and fluoro; and R$^2$ is selected from the group consisting of hydrogen; methyl; ethyl; 1,2,2-trimethyl-propyl; (C$_{1-6}$alkyloxy)C$_{1-3}$alkyl; (C$_{3-8}$cycloalkyl)C$_{1-3}$alkyl; phenyl; phenyl substituted with 1 or 2 substituents each independently selected from the group consisting of C$_{1-3}$alkyl, C$_{1-3}$alkyloxy, fluoro and C$_{1-3}$alkyl substituted with 1, 2 or 3 independently selected fluoro substituents; (phenyl)C$_{1-3}$alkyl; (phenyl)C$_{1-3}$alkyl wherein the phenyl part is substituted with 1 or 2 fluoro substituents; pyridinyl; pyridinyl substituted with 1 or 2 substituents each independently selected from the group consisting of C$_{1-3}$alkyl, C$_{1-3}$alkyloxy, fluoro and C$_{1-3}$alkyl substituted with 1, 2 or 3 independently selected fluoro substituents; and (tetrahydro-2H-pyranyl)-methyl;

and the pharmaceutically acceptable salts and the solvates thereof.

In a particular embodiment, the invention relates to compounds of Formula (I), wherein n is 1 or 2;

A is —CH$_2$O—;

R$^1$ is selected from the group consisting of phenyl and phenyl substituted with 1 or 2 fluoro substituents; and R$^2$ is selected from the group consisting of hydrogen; methyl; ethyl; 1,2,2-trimethyl-propyl; (C$_{1-6}$alkyloxy)C$_{1-3}$alkyl; (C$_{3-8}$cycloalkyl)C$_{1-3}$alkyl; phenyl; phenyl substituted with 1 or 2 substituents each independently selected from the group consisting of $C_{1-3}$alkyloxy and fluoro; pyridinyl; pyridinyl substituted with 1 or 2 substituents each independently selected from the group consisting of $C_{1-3}$alkyl and fluoro; and (tetrahydro-2H-pyranyl)-methyl;

and the pharmaceutically acceptable salts and the solvates thereof.

In a particular embodiment, the invention relates to compounds of Formula (I), wherein n is 1 or 2;
A is —CH$_2$O—;
$R^1$ is selected from the group consisting of phenyl and phenyl substituted with 1 or 2 fluoro substituents; and
$R^2$ is selected from the group consisting of methyl; phenyl; phenyl substituted with 1 or 2 substituents each independently selected from the group consisting of $C_{1-3}$alkyloxy and fluoro; pyridinyl; and pyridinyl substituted with 1 or 2 substituents each independently selected from the group consisting of $C_{1-3}$alkyl and fluoro; and the pharmaceutically acceptable salts and the solvates thereof.

In a particular embodiment, the invention relates to compounds of Formula (I), wherein n is 1 or 2;
A is —CH$_2$O—;
$R^1$ is selected from the group consisting of phenyl and phenyl substituted with 1 or 2 fluoro substituents; and
$R^2$ is selected from the group consisting of methyl; phenyl; phenyl substituted with 1 or 2 substituents each independently selected from the group consisting of methoxy and fluoro; pyridinyl; and pyridinyl substituted with 1 or 2 substituents each independently selected from the group consisting of methyl and fluoro;

and the pharmaceutically acceptable salts and the solvates thereof.

In a particular embodiment, the invention relates to compounds of Formula (I), wherein n is 1;
A is —CH$_2$O—;
$R^1$ is selected from the group consisting of phenyl and phenyl substituted with 1 or 2 fluoro substituents; and
$R^2$ is selected from the group consisting of phenyl; phenyl substituted with 1 or 2 fluoro substituents; and pyridinyl substituted with 1 or 2 substituents each independently selected from the group consisting of methyl and fluoro;

and the pharmaceutically acceptable salts and the solvates thereof.

In a particular embodiment, the invention relates to compounds of Formula (I), wherein n is 2;
A is —CH$_2$O—;
$R^1$ is selected from the group consisting of phenyl and phenyl substituted with 1 or 2 fluoro substituents; and
$R^2$ is selected from the group consisting of methyl; phenyl; and phenyl substituted with 1 or 2 fluoro substituents;

and the pharmaceutically acceptable salts and the solvates thereof.

In a particular embodiment, the invention relates to compounds of Formula (I), wherein n is 1 or 2;
A is —O—CH$_2$—;
$R^1$ is selected from the group consisting of phenyl; phenyl substituted with 1, 2 or 3 substituents each independently selected from the group consisting of $C_{1-3}$alkyl and fluoro; and 3-cyanophenyl; and
$R^2$ is selected from the group consisting of $C_{1-3}$alkyl; ($C_{1-6}$alkyloxy)$C_{1-3}$alkyl; $C_{3-8}$cycloalkyl; ($C_{3-8}$cycloalkyl)$C_{1-3}$alkyl; phenyl; phenyl substituted with 1, 2 or 3 substituents each independently selected from the group consisting of $C_{1-3}$alkyl, $C_{1-3}$alkyloxy, halo and $C_{1-3}$alkyl substituted with 1, 2 or 3 fluoro substituents; (phenyl)$C_{1-3}$alkyl; (phenyl)$C_{1-3}$alkyl wherein the phenyl part is substituted with 1, 2 or 3 independently selected halo substituents; pyridinyl; pyridinyl substituted with 1 or 2 substituents each independently selected from the group consisting of $C_{1-3}$alkyl, $C_{1-3}$alkyloxy, halo and $C_{1-3}$alkyl substituted with 1, 2 or 3 fluoro substituents; and (tetrahydro-2H-pyranyl)-methyl;

and the pharmaceutically acceptable salts and the solvates thereof.

In a particular embodiment, the invention relates to compounds of Formula (I), wherein n is 1 or 2;
A is —O—CH$_2$—;
$R^1$ is selected from the group consisting of phenyl and phenyl substituted with 1 or 2 substituents each independently selected from the group consisting of $C_{1-3}$alkyl and fluoro; and
$R^2$ is selected from the group consisting of $C_{1-3}$alkyl; ($C_{1-6}$alkyloxy)$C_{1-3}$alkyl; ($C_{3-8}$cycloalkyl)$C_{1-3}$alkyl; phenyl; phenyl substituted with 1 or 2 substituents each independently selected from the group consisting of $C_{1-3}$alkyl, $C_{1-3}$alkyloxy, halo and $C_{1-3}$alkyl substituted with 1, 2 or 3 fluoro substituents; (phenyl)$C_{1-3}$alkyl; (phenyl)$C_{1-3}$alkyl wherein the phenyl part is substituted with 1 or 2 independently selected halo substituents; pyridinyl; pyridinyl substituted with 1 or 2 substituents each independently selected from the group consisting of $C_{1-3}$alkyl, $C_{1-3}$alkyloxy, halo and $C_{1-3}$alkyl substituted with 1, 2 or 3 fluoro substituents; and (tetrahydro-2H-pyranyl)methyl;

and the pharmaceutically acceptable salts and the solvates thereof.

In an embodiment, $R^2$ is selected from the group consisting of $C_{1-3}$alkyl; ($C_{1-6}$alkyloxy)$C_{1-3}$alkyl; ($C_{3-8}$cycloalkyl)$C_{1-3}$alkyl; phenyl; phenyl substituted with 1 or 2 substituents each independently selected from the group consisting of $C_{1-3}$alkyl, $C_{1-3}$alkyloxy, halo and $C_{1-3}$alkyl substituted with 1, 2 or 3 fluoro substituents; (phenyl)$C_{1-3}$alkyl; and (phenyl)$C_{1-3}$alkyl wherein the phenyl part is substituted with 1 or 2 independently selected halo substituents; and n, A and $R^1$ are as previously defined.

In a particular embodiment, the invention relates to compounds of Formula (I), wherein n is 1 or 2;
A is —O—CH$_2$—;
$R^1$ is selected from the group consisting of phenyl and phenyl substituted with 1 or 2 substituents each independently selected from the group consisting of $C_{1-3}$alkyl and fluoro; and
$R^2$ is selected from the group consisting of $C_{1-3}$alkyl; phenyl; phenyl substituted with 1 or 2 substituents each independently selected from the group consisting of halo and $C_{1-3}$alkyl substituted with 1, 2 or 3 fluoro substituents; (phenyl)$C_{1-3}$alkyl; and (phenyl)$C_{1-3}$alkyl wherein the phenyl part is substituted with 1 or 2 independently selected halo substituents;

and the pharmaceutically acceptable salts and the solvates thereof.

In a particular embodiment, the invention relates to compounds of Formula (I), wherein n is 1 or 2;
A is —O—CH$_2$—;
$R^1$ is selected from the group consisting of phenyl and phenyl substituted with 1 or 2 substituents each independently selected from the group consisting of methyl and fluoro; and $R^2$ is selected from the group consisting of $C_{1-3}$alkyl; phenyl; phenyl substituted with 1 or 2 substituents each independently selected from the group consisting of fluoro and trifluoromethyl; (phenyl)methyl; and (phenyl)methyl wherein the phenyl part is substituted with 1 or 2 fluoro substituents;

and the pharmaceutically acceptable salts and the solvates thereof.

In a particular embodiment, the invention relates to compounds of Formula (I), wherein n is 1 or 2;

A is —CH$_2$O— or —OCH$_2$—;

$R^1$ is phenyl; and $R^2$ is selected from the group consisting of methyl and 4-fluoro-phenyl;

and the pharmaceutically acceptable salts and the solvates thereof.

In a further embodiment, $R^1$ is selected from the group consisting of phenyl; 2-fluorophenyl; 3-fluorophenyl; 4-fluorophenyl; 2,4-difluorophenyl; 3-methylphenyl; and 3-cyanophenyl; and n, X and $R^2$ are as previously defined.

In a further embodiment, $R^1$ is selected from the group consisting of phenyl; 2-fluorophenyl; 3-fluorophenyl; 4-fluorophenyl; 2,4-difluorophenyl; 3-methylphenyl; and n, X and $R^2$ are as previously defined.

In an additional embodiment, $R^1$ is phenyl optionally substituted with 1 or 2 substituents each independently selected from the group consisting of $C_{1-3}$alkyl and fluoro.

In an additional embodiment, $R^1$ is phenyl optionally substituted with 1 or 2 fluoro substituents.

In another embodiment, $R^1$ is selected from the group consisting of phenyl; 2-fluorophenyl; 3-fluorophenyl; and 4-fluorophenyl.

In a further embodiment, $R^2$ is selected from the group consisting of hydrogen; methyl; ethyl; 1,2,2-trimethyl-propyl; 2-methoxyethyl; cyclopropyl; (cyclopropyl)methyl; phenyl; 3-fluorophenyl; 4-fluorophenyl; 2,4-difluorophenyl; (phenyl)methyl; 3-trifluoromethylphenyl; 4-trifluoromethylphenyl; 2-methoxyphenyl; (2-fluorophenyl)methyl; (3-fluorophenyl)methyl; (4-fluorophenyl)methyl; (2,4-difluorophenyl)methyl; 2-pyridinyl; 3-methyl-2-pyridinyl; 4-methyl-2-pyridinyl; 5-methyl-2-pyridinyl; 6-methyl-2-pyridinyl; 5-fluoro-2-pyridinyl; 3-pyridinyl; 4-pyridinyl; 3-fluoro-2-pyridinyl; 5-fluoro-3-pyridinyl; 3-fluoro-4-pyridinyl; and (tetrahydro-2H-pyran-4-yl)methyl.

In a further embodiment, $R^2$ is selected from the group consisting of hydrogen; methyl; ethyl; 1,2,2-trimethyl-propyl; 2-methoxyethyl; (cyclopropyl)methyl; phenyl; 3-fluorophenyl; 4-fluorophenyl; 2,4-difluorophenyl; (phenyl)methyl; 3-trifluoromethylphenyl; 4-trifluoromethylphenyl; 2-methoxyphenyl; (2-fluorophenyl)methyl; (3-fluorophenyl)methyl; (4-fluorophenyl)methyl; (2,4-difluorophenyl)methyl; 2-pyridinyl; 3-methyl-2-pyridinyl; 4-methyl-2-pyridinyl; 5-methyl-2-pyridinyl; 6-methyl-2-pyridinyl; 5-fluoro-2-pyridinyl; 3-pyridinyl; 4-pyridinyl; 3-fluoro-2-pyridinyl; 5-fluoro-3-pyridinyl; 3-fluoro-4-pyridinyl; and (tetrahydro-2H-pyran-4-yl)methyl.

In an additional embodiment, $R^2$ is selected from the group consisting of hydrogen; methyl; ethyl; 1,2,2-trimethyl-propyl; 2-methoxyethyl; (cyclopropyl)methyl; 4-fluorophenyl; 2,4-difluorophenyl; 2-methoxyphenyl; 2-pyridinyl; 3-methyl-2-pyridinyl; 4-methyl-2-pyridinyl; 5-methyl-2-pyridinyl; 6-methyl-2-pyridinyl; 5-fluoro-2-pyridinyl; 3-pyridinyl; 4-pyridinyl; 3-fluoro-2-pyridinyl; 5-fluoro-3-pyridinyl; 3-fluoro-4-pyridinyl; and (tetrahydro-2H-pyran-4-yl)methyl.

In an additional embodiment, $R^2$ is selected from the group consisting of $C_{1-3}$alkyl; phenyl; phenyl substituted with 1 or 2 substituents each independently selected from the group consisting of fluoro and trifluoromethyl; (phenyl)methyl; and (phenyl)methyl wherein the phenyl part is substituted with 1 or 2 fluoro substituents;

and n, X and $R^1$ are as previously defined.

In a further embodiment, A is —CH$_2$O—.

In a further embodiment, A is —OCH$_2$—.

In a further embodiment, A is —OCH$_2$— and n is 1.

In a further embodiment, $R^2$ is methyl.

In a further embodiment, $R^2$ is 4-fluorophenyl.

In an embodiment, halo represents fluoro in each definition.

In yet another preferred embodiment, $R^2$ is selected from the group consisting of methyl; methoxyethyl; 4-fluorophenyl; 2,4-difluorophenyl; (phenyl)methyl; 2-fluorophenylmethyl; 3-fluorophenylmethyl; 4-fluorophenylmethyl; and 2,4-difluorophenylmethyl.

All possible combinations of the above-indicated interesting embodiments are considered to be embraced within the scope of this invention.

Particular compounds may be selected from the group of 5-(4-fluorophenyl)-6,7-dihydro-2-(phenylmethoxy)-thiazolo[5,4-c]pyridin-4(5H)-one, 6,7-dihydro-2-(phenoxymethyl)-thiazolo[5,4-c]pyridin-4 (5H)-one, 6,7-dihydro-2-(phenoxymethyl)-5-[(tetrahydro-2H-pyran-4-yl)methyl]-thiazolo[5,4-c]pyridin-4(5H)-one, 6,7-dihydro-5-(2-methoxyethyl)-2-(phenoxymethyl)-thiazolo[5,4-c]pyridin-4(5H)-one, 6,7-dihydro-5-(5-methyl-2-pyridinyl)-2-(phenoxymethyl)-thiazolo[5,4-c]pyridin-4(5H)-one, 2-[(4-fluorophenoxy)methyl]-5-(4-fluorophenyl)-6,7-dihydro-thiazolo[5,4-c]pyridin-4(5H)-one, 2-[(3-fluorophenoxy)methyl]-6,7-dihydro-5-[(1R)-1,2,2-trimethylpropyl]-thiazolo[5,4-c]pyridin-4(5H)-one, 6,7-dihydro-5-methyl-2-(phenoxymethyl)-thiazolo[5,4-c]pyridin-4(5H)-one, 5-(4-fluorophenyl)-6,7-dihydro-2-(phenoxymethyl)-thiazolo[5,4-c]pyridin-4(5H)-one, 5,6,7,8-tetrahydro-2-(phenoxymethyl)-4H-thiazolo[5,4-c]azepin-4-one, 5-(4-fluorophenyl)-5,6,7,8-tetrahydro-2-(phenoxymethyl)-4H-thiazolo[5,4-c]azepin-4-one, 5-(2,4-difluorophenyl)-6,7-dihydro-2-(phenylmethoxy)-thiazolo[5,4-c]pyridin-4(5H)-one, 5-[(2,4-difluorophenyl)methyl]-6,7-dihydro-2-(phenylmethoxy)-thiazolo[5,4-c]pyridin-4(5H)-one, 5-[(4-fluorophenyl)methyl]-6,7-dihydro-2-(phenylmethoxy)-thiazolo[5,4-c]pyridin-4(5H)-one, 5-[(3-fluorophenyl)methyl]-6,7-dihydro-2-(phenylmethoxy)-thiazolo[5,4-c]pyridin-4(5H)-one, 5-[(2-fluorophenyl)methyl]-6,7-dihydro-2-(phenylmethoxy)-thiazolo[5,4-c]pyridin-4(5H)-one, 5-(2,4-difluorophenyl)-2-[(3-fluorophenyl)methoxy]-6,7-dihydro-thiazolo[5,4-c]pyridin-4(5H)-one, 5-(2,4-difluorophenyl)-2-[(2-fluorophenyl)methoxy]-6,7-dihydro-thiazolo[5,4-c]pyridin-4(5H)-one, 5-(4-fluorophenyl)-2-[(3-fluorophenyl)methoxy]-6,7-dihydro-thiazolo[5,4-c]pyridin-4(5H)-one, 3-[[[5-(2,4-difluorophenyl)-4,5,6,7-tetrahydro-4-oxothiazolo[5,4-c]pyridin-2-yl]oxy]methyl]-benzonitrile, 5-(2,4-difluorophenyl)-6,7-dihydro-2-[(3-methylphenyl)methoxy]-thiazolo[5,4-c]pyridin-4(5H)-one, 5-(4-fluorophenyl)-2-[(2-fluorophenyl)methoxy]-6,7-dihydro-thiazolo[5,4-c]pyridin-4(5H)-one, 5-(2,4-difluorophenyl)-2-[(2,4-difluorophenyl)methoxy]-6,7-dihydro-thiazolo[5,4-c]pyridin-4(5H)-one, 6,7-dihydro-5-methyl-2-(phenylmethoxy)-thiazolo[5,4-c]
pyridin-4(5H)-one,
2-[(3-fluorophenoxy)methyl]-5-(4-fluorophenyl)-6,7-dihydro-thiazolo[5,4-c]pyridin-4(5H)-one,
2-[(3-fluorophenyl)methoxy]-6,7-dihydro-5-[4-(trifluoromethyl)phenyl]-thiazolo[5,4-c]pyridin-4(5H)-one,
5-(3-fluorophenyl)-2-[(3-fluorophenyl)methoxy]-6,7-dihydro-thiazolo[5,4-c]pyridin-4(5H)-one,
5-(2,4-difluorophenyl)-2-[(3-fluorophenoxy)methyl]-6,7-dihydro-thiazolo[5,4-c]pyridin-4(5H)-one,
5-(2,4-difluorophenyl)-6,7-dihydro-2-(phenoxymethyl)-thiazolo[5,4-c]pyridin-4(5H)-one,
2-[(3-fluorophenyl)methoxy]-6,7-dihydro-5-[3-(trifluoromethyl)phenyl]-thiazolo[5,4-c]pyridin-4(5H)-one,
2-[(2-fluorophenoxy)methyl]-5-(4-fluorophenyl)-6,7-dihydro-thiazolo[5,4-c]pyridin-4(5H)-one,
5-(2,4-difluorophenyl)-2-[(4-fluorophenoxy)methyl]-6,7-dihydro-thiazolo[5,4-c]pyridin-4(5H)-one,
2-[(2-fluorophenoxy)methyl]-6,7-dihydro-5-[(1R)-1,2,2-trimethylpropyl]-thiazolo[5,4-c]pyridin-4(5H)-one,
2-[(4-fluorophenoxy)methyl]-6,7-dihydro-5-[(1R)-1,2,2-trimethylpropyl]-thiazolo[5,4-c]pyridin-4(5H)-one,
6,7-dihydro-2-(phenoxymethyl)-5-[(1R)-1,2,2-trimethylpropyl]-thiazolo[5,4-c]pyridin-4(5H)-one,
2-[(2-fluorophenoxy)methyl]-6,7-dihydro-5-(2-methoxyphenyl)-thiazolo[5,4-c]pyridin-4(5H)-one,
2-[(3-fluorophenoxy)methyl]-6,7-dihydro-5-(2-methoxyphenyl)-thiazolo[5,4-c]pyridin-4(5H)-one,
5,6,7,8-tetrahydro-5-methyl-2-(phenoxymethyl)-4H-thiazolo[5,4-c]azepin-4-one,
5-(cyclopropylmethyl)-6,7-dihydro-2-(phenoxymethyl)-thiazolo[5,4-c]pyridin-4(5H)-one,
5-cyclopropyl-2-[(3-fluorophenoxy)methyl]-6,7-dihydro-thiazolo[5,4-c]pyridin-4(5H)-one,
5-(cyclopropylmethyl)-2-[(3-fluorophenoxy)methyl]-6,7-dihydro-thiazolo[5,4-c]pyridin-4(5H)-one,
5-(cyclopropylmethyl)-2-[(2-fluorophenoxy)methyl]-6,7-dihydro-thiazolo[5,4-c]pyridin-4(5H)-one,
5-(cyclopropylmethyl)-2-[(4-fluorophenoxy)methyl]-6,7-dihydro-thiazolo[5,4-c]pyridin-4(5H)-one,
5-cyclopropyl-6,7-dihydro-2-(phenoxymethyl)-thiazolo[5,4-c]pyridin-4(5H)-one,
6,7-dihydro-2-(phenoxymethyl)-5-(2-pyridinyl)-thiazolo[5,4-c]pyridin-4(5H)-one,
6,7-dihydro-5-(6-methyl-2-pyridinyl)-2-(phenoxymethyl)-thiazolo[5,4-c]pyridin-4(5H)-one,
5-(5-fluoro-2-pyridinyl)-6,7-dihydro-2-(phenoxymethyl)-thiazolo[5,4-c]pyridin-4(5H)-one,
6,7-dihydro-2-(phenoxymethyl)-5-(3-pyridinyl)-thiazolo[5,4-c]pyridin-4(5H)-one,
6,7-dihydro-2-(phenoxymethyl)-5-(4-pyridinyl)-thiazolo[5,4-c]pyridin-4(5H)-one,
5-(3-fluoro-2-pyridinyl)-6,7-dihydro-2-(phenoxymethyl)-thiazolo[5,4-c]pyridin-4(5H)-one,
6,7-dihydro-5-(4-methyl-2-pyridinyl)-2-(phenoxymethyl)-thiazolo[5,4-c]pyridin-4(5H)-one,
6,7-dihydro-5-(3-methyl-2-pyridinyl)-2-(phenoxymethyl)-thiazolo[5,4-c]pyridin-4(5H)-one,
2-[(4-fluorophenoxy)methyl]-5-(5-fluoro-2-pyridinyl)-6,7-dihydro-thiazolo[5,4-c]pyridin-4(5H)-one,
2-[(3-fluorophenoxy)methyl]-5-(5-fluoro-2-pyridinyl)-6,7-dihydro-thiazolo[5,4-c]pyridin-4(5H)-one,
2-[(2-fluorophenoxy)methyl]-5-(5-fluoro-2-pyridinyl)-6,7-dihydro-thiazolo[5,4-c]pyridin-4(5H)-one,
5-ethyl-6,7-dihydro-2-(phenoxymethyl)-thiazolo[5,4-c]pyridin-4(5H)-one,
5-(5-fluoro-3-pyridinyl)-6,7-dihydro-2-(phenoxymethyl)-thiazolo[5,4-c]pyridin-4(5H)-one,
5-(3-fluoro-4-pyridinyl)-6,7-dihydro-2-(phenoxymethyl)-thiazolo[5,4-c]pyridin-4(5H)-one,
5-(2,4-difluorophenyl)-2-[(2-fluorophenoxy)methyl]-6,7-dihydro-thiazolo[5,4-c]pyridin-4(5H)-one,
2-[(4-chlorophenoxy)methyl]-5-(4-fluorophenyl)-6,7-dihydro-thiazolo[5,4-c]pyridin-4(5H)-one,
5-cyclopropyl-2-[(2-fluorophenoxy)methyl]-6,7-dihydro-thiazolo[5,4-c]pyridin-4(5H)-one,
5-cyclopropyl-2-[(4-fluorophenoxy)methyl]-6,7-dihydro-thiazolo[5,4-c]pyridin-4(5H)-one,
6,7-dihydro-5-(1-methylethyl)-2-(phenoxymethyl)-thiazolo[5,4-c]pyridin-4(5H)-one,
2-[(3-fluorophenoxy)methyl]-6,7-dihydro-5-(1-methylethyl)-thiazolo[5,4-c]pyridin-4(5H)-one,
6,7-dihydro-2-(phenylmethoxy)-thiazolo[5,4-c]pyridin-4(5H)-one,
2-fluoro-5-[[(4,5,6,7-tetrahydro-4-oxothiazolo[5,4-c]pyridin-2-yl)oxy]methyl]-benzonitrile,
6,7-dihydro-2-[(2-methylphenyl)methoxy]-thiazolo[5,4-c]pyridin-4(5H)-one,
6,7-dihydro-2-[(3-methylphenyl)methoxy]-thiazolo[5,4-c]pyridin-4(5H)-one,
2-[(2-fluorophenyl)methoxy]-6,7-dihydro-thiazolo[5,4-c]pyridin-4(5H)-one,
2-[(2-fluorophenyl)methoxy]-6,7-dihydro-thiazolo[5,4-c]pyridin-4(5H)-one trifluoroacetate,
2-[(3-fluorophenyl)methoxy]-6,7-dihydro-thiazolo[5,4-c]pyridin-4(5H)-one,
2-[(3-fluorophenyl)methoxy]-6,7-dihydro-thiazolo[5,4-c]pyridin-4(5H)-one trifluoroacetate,
2-[(4-fluorophenyl)methoxy]-6,7-dihydro-thiazolo[5,4-c]pyridin-4(5H)-one,
2-[(4-fluorophenyl)methoxy]-6,7-dihydro-thiazolo[5,4-c]pyridin-4(5H)-one trifluoroacetate,
6,7-dihydro-2-[(4-methylphenyl)methoxy]-thiazolo[5,4-c]pyridin-4(5H)-one,
5-(2,4-difluorophenyl)-2-[(3,5-difluorophenyl)methoxy]-6,7-dihydro-thiazolo[5,4-c]pyridin-4(5H)-one,
5-(2,4-difluorophenyl)-2-[(3,4-difluorophenyl)methoxy]-6,7-dihydro-thiazolo[5,4-c]pyridin-4(5H)-one,
4-[[[5-(2,4-difluorophenyl)-4,5,6,7-tetrahydro-4-oxothiazolo[5,4-c]pyridin-2-yl]oxy]methyl]-benzonitrile,
2-[[[5-(2,4-difluorophenyl)-4,5,6,7-tetrahydro-4-oxothiazolo[5,4-c]pyridin-2-yl]oxy]methyl]-benzonitrile,
2-[(3-fluorophenyl)methoxy]-6,7-dihydro-5-[(1R)-1,2,2-trimethylpropyl]-thiazolo[5,4-c]pyridin-4(5H)-one,
5-(2,4-difluorophenyl)-6,7-dihydro-2-[[4-(trifluoromethyl)phenyl]methoxy]-thiazolo[5,4-c]pyridin-4(5H)-one,
5-(2,4-difluorophenyl)-6,7-dihydro-2-[(2-methoxyphenyl)methoxy]-thiazolo[5,4-c]pyridin-4(5H)-one,
5-(2,4-difluorophenyl)-6,7-dihydro-2-[(3-methoxyphenyl)methoxy]-thiazolo[5,4-c]pyridin-4(5H)-one, and
5-(2,4-difluorophenyl)-6,7-dihydro-2-[[2-(trifluoromethyl)phenyl]methoxy]-thiazolo[5,4-c]pyridin-4(5H)-one,
and the stereoisomeric forms, pharmaceutically acceptable salts and solvates thereof.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable salts are defined to comprise the therapeutically active non-toxic acid addition salt forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid. Conversely said salt forms can be converted into the free base form by treatment with an appropriate base.

The compounds according to Formula (I) containing acidic protons may also be converted into their therapeutically active non-toxic base salt forms by treatment with appropriate organic and inorganic bases. Appropriate base salt forms comprise, for example, the ammonium salts, the alkaline and earth alkaline metal salts, in particular lithium, sodium, potassium, magnesium and calcium salts, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids, for example arginine and lysine.

Conversely, said salt forms can be converted into the free acid forms by treatment with an appropriate acid.

The term solvate comprises the solvent addition forms as well as the salts thereof, which the compounds of Formula (I) are able to form. Examples of such solvent addition forms are e.g. hydrates, alcoholates and the like.

The term "stereochemically isomeric forms" or "stereoisomeric forms" as used hereinbefore or hereinafter, defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. The invention also embraces each of the individual isomeric forms of the compounds of Formula (I) and their salts and solvates, substantially free, i.e. associated with less than 50%, preferably less than 20%, more preferably less than 10%, preferably less than 5%, in particular less than 2% and most preferably less than 1% of the other isomers. Thus, when a compound of Formula (I) is for instance specified as (R), this means that the compound is substantially free of the (S) isomer. Stereogenic centers may have the R- or S-configuration; substituents on bivalent cyclic (partially) saturated radicals may have either the cis- or trans-configuration. Compounds encompassing double bonds can have an E- or Z-stereochemistry at said double bond. Stereisomeric forms of the compounds of Formula (I) are embraced within the scope of this invention.

Following CAS nomenclature conventions, when two stereogenic centers of known absolute configuration are present in a compound, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the compound has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{3}H$, $^{11}C$ and $^{18}F$.

Preparation

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

A. Preparation of the Final Compounds

Experimental Procedure 1

Compounds according to Formula (I), wherein A is —O—CH$_2$—, hereby named (I-a), can be prepared by reacting an intermediate of Formula (II) with an alcohol of Formula (III) according to Reaction Scheme (1). The reaction is performed in a suitable reaction-inert solvent, such as, for example acetonitrile, in the presence of a suitable base, such as, for example Cs$_2$CO$_3$, under thermal conditions such as, for example heating the reaction mixture at 80° C. for a period of time to allow completion of the reaction, for example overnight. Alternative reaction conditions can be selected by the person skilled in the art from reaction procedures well described in the literature. In Reaction Scheme (1), all variables are as defined in Formula (I).

Reaction Scheme 1

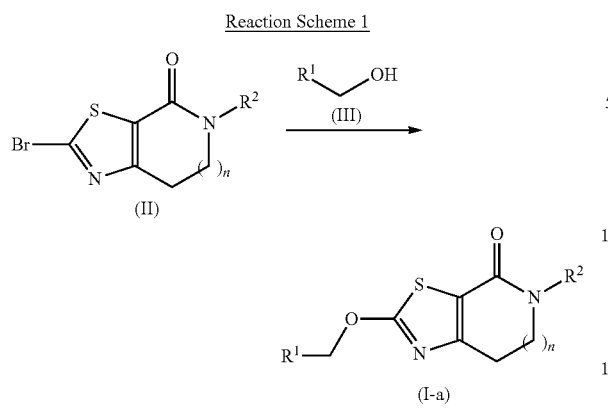

A compound of Formula (III) can be obtained commercially.

Experimental Procedure 2

Compounds according to Formula (I), wherein A is —$CH_2$—O—, hereby named (I-b) can be prepared by a Mitsunobu type reaction between an intermediate of Formula (IV) with an appropriate alcohol of Formula (V), in the presence of a trialkyl or triaryl phosphine, such as for example, triphenylphosphine, and a dialkyl azodicarboxylate reagent, such as for example, di-tert-butyl azodicarboxylate (DTBAD) according to Reaction Scheme (2a). The reaction is performed in a suitable reaction-inert solvent, such as, for example, tetrahydrofuran, under thermal conditions such as, for example, heating the reaction mixture at 120° C., for a period of time to allow completion of the reaction, for example 20 minutes. In Reaction Scheme (2a), all variables are as defined in Formula (I).

Reaction Scheme 2a

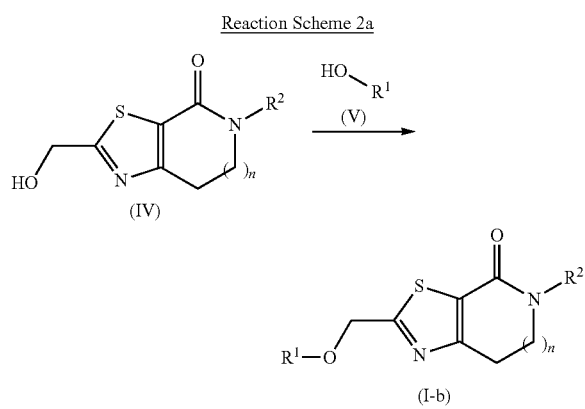

Alternatively, compounds according to Formula (I-b) can be prepared by a reaction between an intermediate of Formula (VI) with an appropriate alcohol of Formula (V), according to Reaction Scheme (2b). The reaction is performed in a suitable reaction-inert solvent, such as, for example, acetonitrile, in the presence of a suitable base, such as, for example, $Cs_2CO_3$ under thermal conditions such as, for example, heating the reaction mixture at 80° C. for a period of time to allow completion of the reaction, for example overnight. Alternative reaction conditions can be selected by the person skilled in the art from reaction procedures well described in the literature. In Reaction Scheme (2b), all variables are as defined in Formula (I).

Reaction Scheme 2a

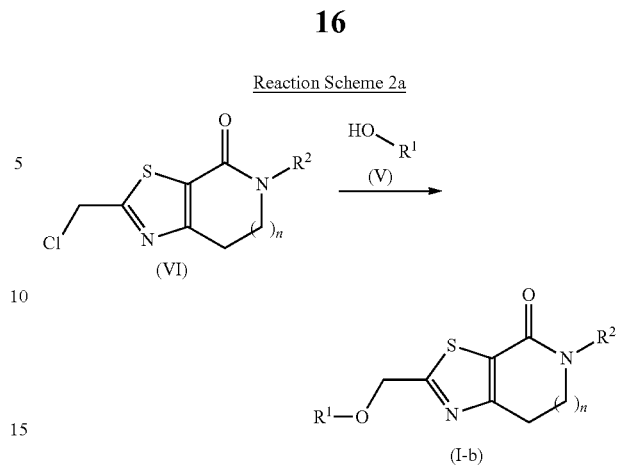

A compound of Formula (V) can be obtained commercially.

Compounds according to Formula (I-b) can also be prepared by reaction of an intermediate of Formula (VII) with an appropriate thioacetamide of Formula (VIII) according to Reaction Scheme (2c). The reaction is performed in a reaction-inert solvent, such as for example ethanol, at a moderately high temperature, such as for example 80° C. for a period of time that allows completion of the reaction. In Reaction Scheme (2c), all variables are as defined in Formula (I).

Reaction Scheme 2c

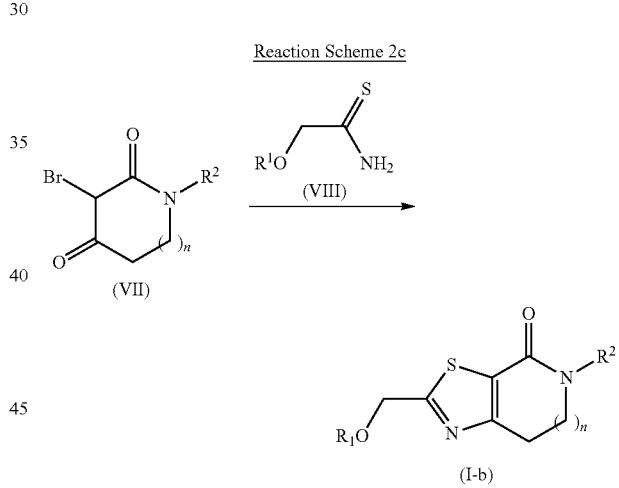

A compound of Formula (VIII) can be prepared according to the procedure described in WO 2007/056366 A2 (2007 May 18) or alternatively can be obtained commercially.

Experimental Procedure 3

Compounds according to Formula (I-b), can be prepared by a coupling reaction between a compound of Formula (I-b) wherein $R^2$ is hydrogen, hereby named (I-b') with a reagent of Formula (IX) according to Reaction Scheme (3). The reaction is performed in a suitable reaction-inert solvent, such as, for example toluene, in the presence of a suitable base, such as, for example $Na_2CO_3$, in the presence of a ligand such as for example N,N'-dimethylethylenediamine, in the presence of a copper salt such as, for example copper iodide, under thermal conditions such as, for example heating the reaction mixture at 120° C. for a period of time to allow completion of the reaction, for example overnight. Alternatively, the reaction could also be performed in a suitable reaction-inert solvent, such as, for example acetonitrile, in the presence of a suitable base, such as for example, $Cs_2CO_3$, under thermal conditions such as heating the reaction mixture at 80° C. or the reaction could also be performed in a suitable reaction-inert solvent, such as, for example N,N-dimethylformamide in the presence of a suitable base such as sodium hydride at low temperature such as 0° C., for a period of time to allow completion of the reaction, for example overnight. Alternatively, reaction conditions can be selected by the person skilled in the art from reaction procedures well described in the literature. In Reaction Scheme (3), all variables are as defined in Formula (I) and Q is a group such as halo.

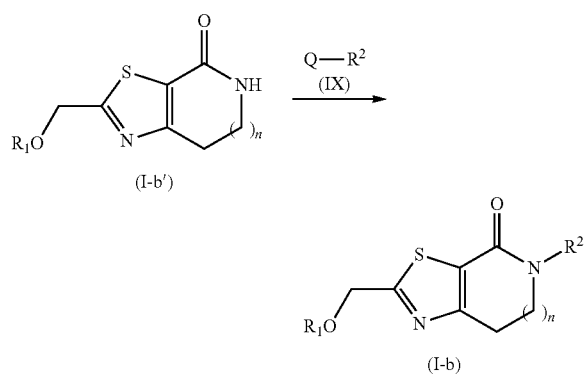

A halo compound of Formula (IX) can be obtained commercially.

B. Preparation of the Intermediate Compounds

Experimental Procedure (4)

Intermediates according to Formula (VI), can be prepared by chlorination of an intermediate of formula (IV) under conditions known to the skilled person, for example, using thionyl chloride, under standard conditions, according to Reaction Scheme (4), wherein all variables are as defined in Formula (I).

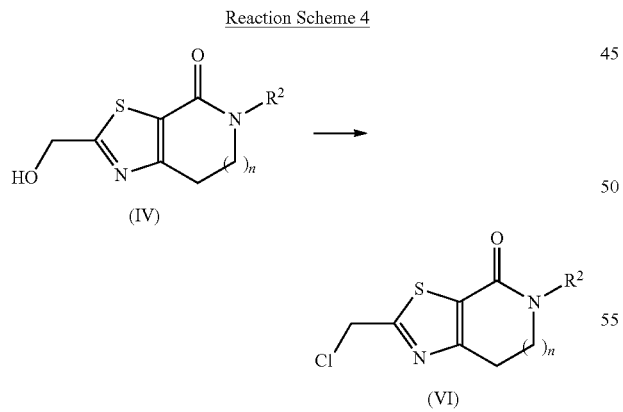

Experimental Procedure 5

Intermediates according to Formula (IV), can be prepared by reduction of an intermediate of Formula (X-a) or an intermediate of Formula (X-b) under conditions known to the skilled person, for example, using sodium borohydride, according to Reaction Scheme (5), wherein all variables are as defined in Formula (I).

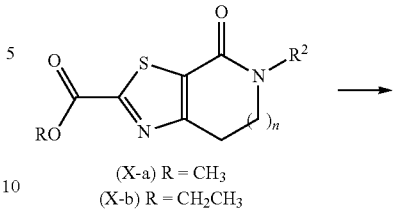

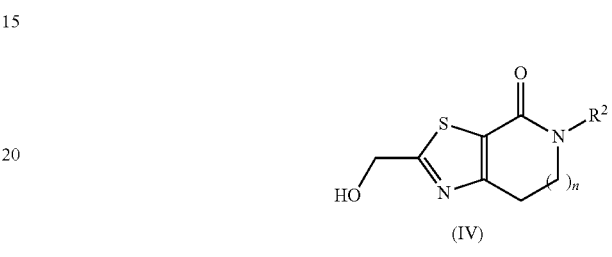

Experimental Procedure 6

Intermediates according to Formula (X-a) or (X-b), can be prepared by carbonylation of an intermediate of Formula (II) under conditions known to the skilled person, for example, using carbon monoxide, an appropriate alcohol such as methanol or ethanol, respectively, and a base, such as for example triethylamine in the presence of a palladium catalyst, such as palladium dichloride, under standard conditions, according to Reaction Scheme (6a), wherein all variables are as defined in Formula (I).

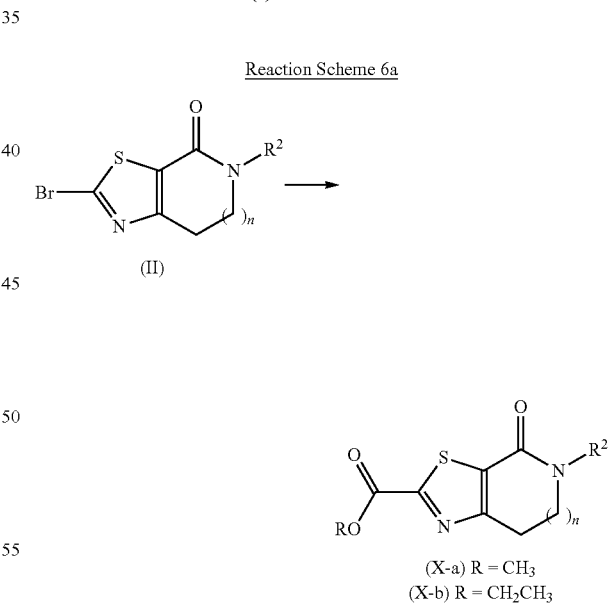

Alternatively, a compound of Formula (X-a) wherein $R^2$ is methyl hereby named (X-a") can be prepared by reaction of a compound of Formula (X-a) wherein $R^2$ is hydrogen hereby named (X-a') with an alkylating reagent such as methyl iodide in the presence of a base, such as cesium carbonate, in an inert solvent such as N,N-dimethylformamide, applying reaction conditions that are known to a person skilled in the art. In Reaction Scheme (6b), all variables are as defined in Formula (I).

Reaction Scheme 6b

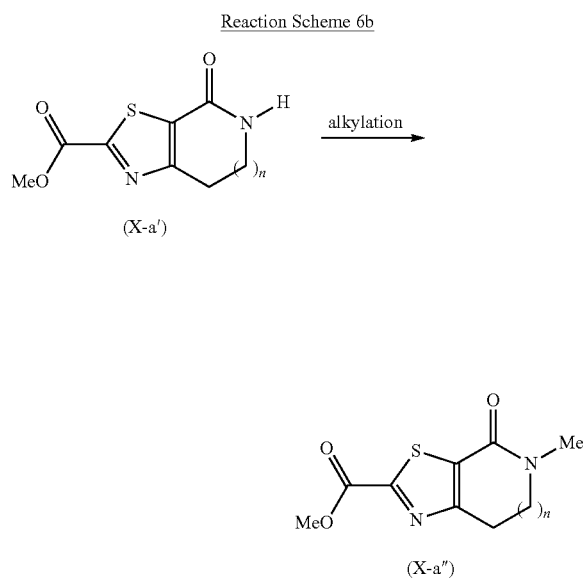

Experimental Procedure 7

The intermediates according to Formula (II) can be prepared by reaction of an intermediate of Formula (XI) according to Reaction Scheme (7). The reaction is performed with a reagent or mixture of reagents suitable for the transformation of an NH$_2$ group into a halogen atom, such as for example a mixture of copper (II) bromide and 3-methyl-1-nitrosooxy-butane, applying reaction conditions that are known to a person skilled in the art. In Reaction Scheme (7), all variables are as defined in Formula (I).

Reaction Scheme 7

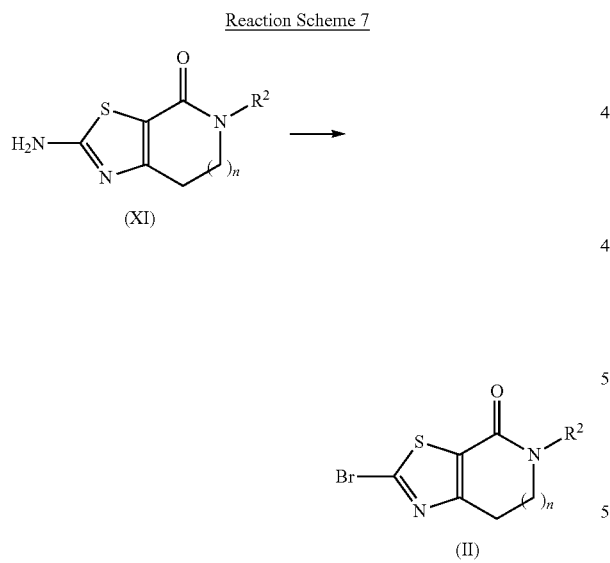

Experimental Procedure 8

The intermediates according to Formula (XI), wherein n is 1, hereby named (XI-a) can be prepared by reaction of an intermediate of Formula (XII) with thiourea according to Reaction Scheme (8). The reaction is performed in a reaction-inert solvent, such as for example ethanol, at a moderately high temperature, such as for example 80° C. for a period of time that allows completion of the reaction. In Reaction Scheme (8), all variables are as defined in Formula (I).

Reaction Scheme 8

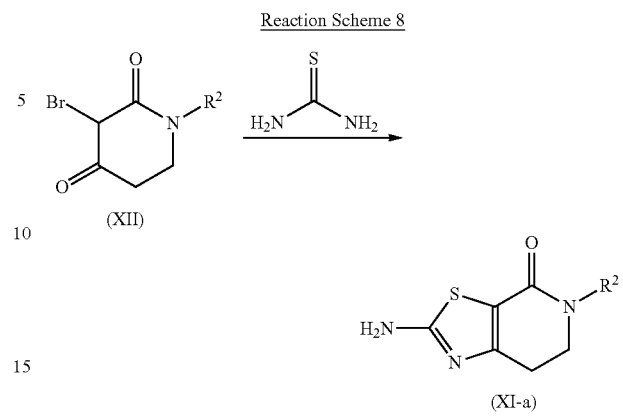

Experimental Procedure 9

Alternatively a compound according to Formula (X-b) can be prepared by bromination of an intermediate of Formula (XII) with ethyl thiooxamate according to Reaction Scheme (9). The reaction is performed in a reaction-inert solvent, such as for example ethanol, with a suitable base, such as for example sodium hydrogencarbonate, at a moderately high temperature, such as for example 80° C. for a period of time that allows completion of the reaction. In Reaction Scheme (9), all variables are as defined in Formula (I).

Reaction Scheme 9

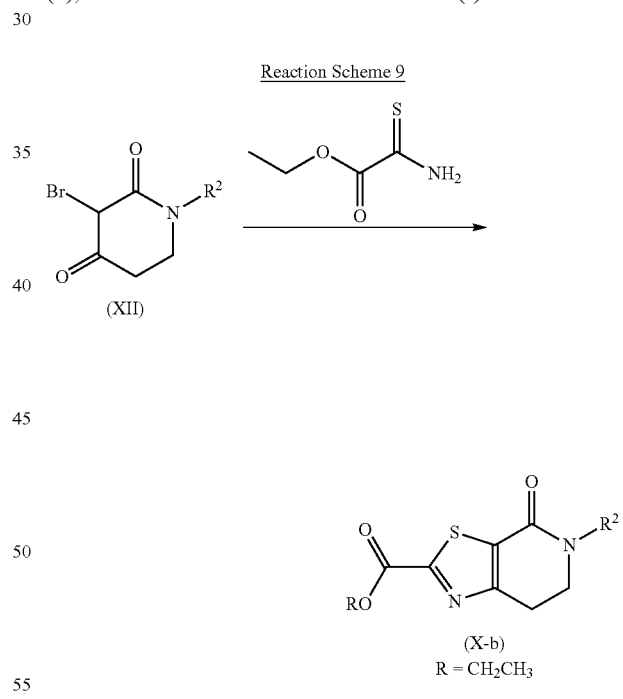

Experimental Procedure 10

The intermediates according to Formula (XII) can be prepared by bromination of an intermediate of Formula (XIII) according to Reaction Scheme (10). The reaction is performed in a reaction-inert solvent, such as for example carbon tetrachloride, with a suitable brominating agent, such as for example N-bromosuccinimide, at a moderately low temperature, such as for example 10° C.-15° C. for a period of time that allows completion of the reaction. In Reaction Scheme (10), all variables are as defined in Formula (I).

Reaction Scheme 10

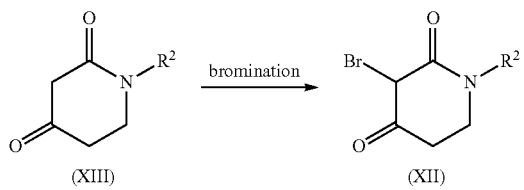

Experimental Procedure 11

The intermediates according to Formula (XIII) can be prepared by decarboxylation of an intermediate of Formula (XIV) according to Reaction Scheme (11). The reaction is performed in a reaction-inert solvent, such as for example water, with a suitable acidic agent, such as for example acetic acid, at a moderately high temperature such as 100° C., for a period of time that allows completion of the reaction. In Reaction Scheme (11), all variables are as defined in Formula (I).

Reaction Scheme 11

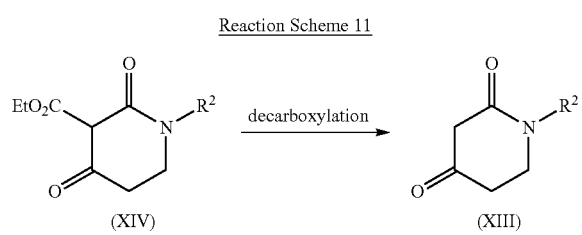

Experimental Procedure 12

The intermediates according to Formula (XIV) can be prepared by reaction of an intermediate of Formula (XV) according to Reaction Scheme (12). The reaction is performed in a reaction-inert solvent, such as for example ethanol, with a suitable base, such as for example sodium ethoxide, at a moderately high temperature such as 85° C., for a period of time that allows completion of the reaction. In Reaction Scheme (12), all variables are as defined in Formula (I).

Reaction Scheme 12

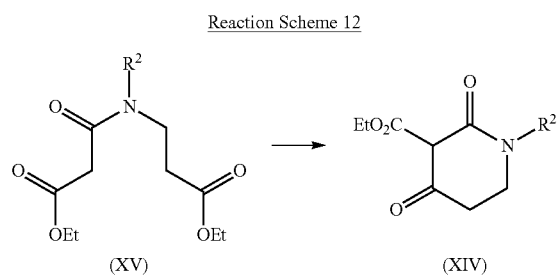

Experimental Procedure 13

The intermediates according to Formula (XV) can be prepared by reaction of an intermediate of Formula (XVI) with ethyl malonyl chloride according to Reaction Scheme (13). The reaction is performed in a reaction-inert solvent, such as for example dichloromethane, with a suitable base, such as for example triethylamine, at a low temperature such as 0° C., for a period of time that allows completion of the reaction. In Reaction Scheme (13), all variables are as defined in Formula (I).

Reaction Scheme 13

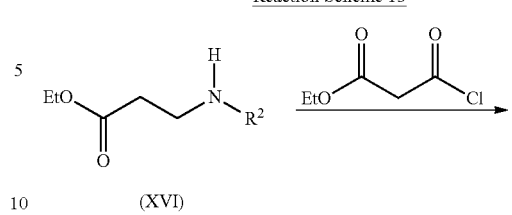

Experimental Procedure 14

The intermediates according to Formula (XVI) can be prepared by reaction of the appropriate amine of Formula (XVII) with ethyl acrylate according to Reaction Scheme (14). The reaction is performed in a reaction-inert solvent, such as for example ethanol, with a suitable acid, such as for example hydrochloric acid, at a high temperature such as 90° C., for a period of time that allows completion of the reaction. In Reaction Scheme (14), all variables are as defined in Formula (I).

Reaction Scheme 14

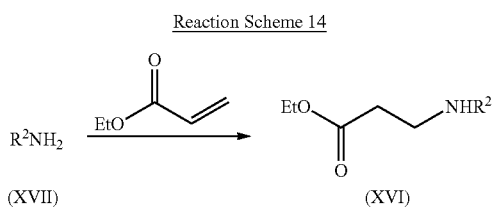

An amine of Formula (XVII) can be obtained commercially.

Experimental Procedure 15

The intermediates according to Formula (XI), wherein $R^2$ is hydrogen and n is 1 hereby named (XI-b), can be prepared from an intermediate of Formula (XVIII) according to Reaction Scheme (15). The reaction is performed with a suitable reagent for the cleavage of the tert-butoxycarbonyl group such as for example hydrochloric acid, applying reaction conditions that are known to a person skilled in the art. In Reaction Scheme (15), all variables are as defined in Formula (I).

Reaction Scheme 15

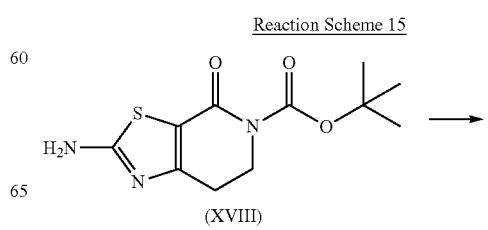

-continued

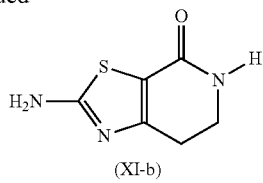

(XI-b)

Experimental Procedure 16

The intermediates according to Formula (XVIII) can be prepared by reaction of an intermediate of Formula (XIX) with thiourea according to Reaction Scheme (16). The reaction is performed in a reaction-inert solvent, such as for example ethanol, at a moderately high temperature, such as for example 80° C. for a period of time that allows completion of the reaction. In Reaction Scheme (16), all variables are as defined in Formula (I).

Reaction Scheme 16

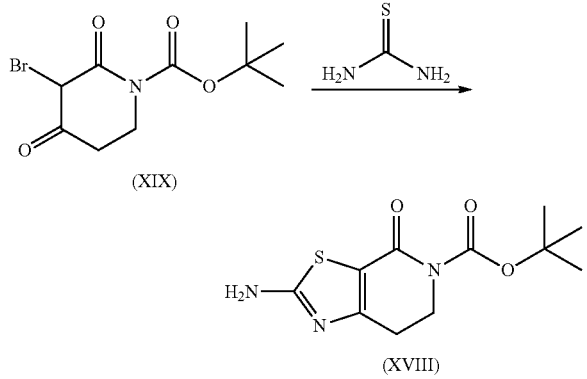

(XIX)

(XVIII)

Experimental Procedure 17

The intermediates according to Formula (XIX) can be prepared by bromination of an intermediate of Formula (XX) according to Reaction Scheme (17). The reaction is performed in a reaction-inert solvent, such as for example carbon tetrachloride, with a suitable brominating reagent, such as for example N-bromosuccinimide, at a moderately low temperature, such as for example 10° C.-15° C. for a period of time that allows completion of the reaction. In Reaction Scheme (17), all variables are as defined in Formula (I).

Reaction Scheme 17

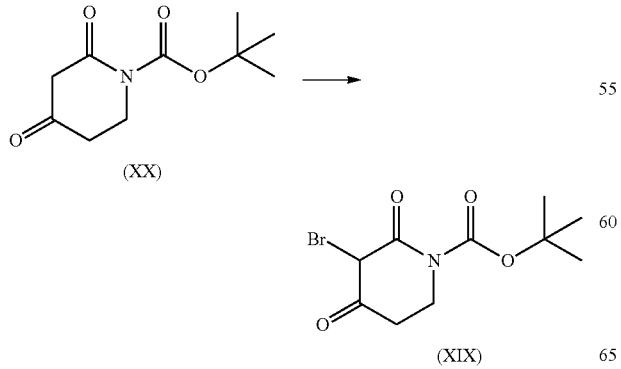

(XX)

(XIX)

A compound of Formula (XX) can be obtained commercially.

Experimental Procedure 18

Compounds according to Formula (I-b) wherein $R^2$ is hydrogen and n is 2 hereby named (I-b") can be prepared by a deprotection reaction of an intermediate of Formula (XXI) with ammonium cerium (IV) nitrate according to Reaction Scheme (18). The reaction is performed in a reaction-inert solvent, such as for example acetonitrile and water, applying reaction conditions that are known to a person skilled in the art. In Reaction Scheme (18), all variables are as defined in Formula (I).

Reaction Scheme 18

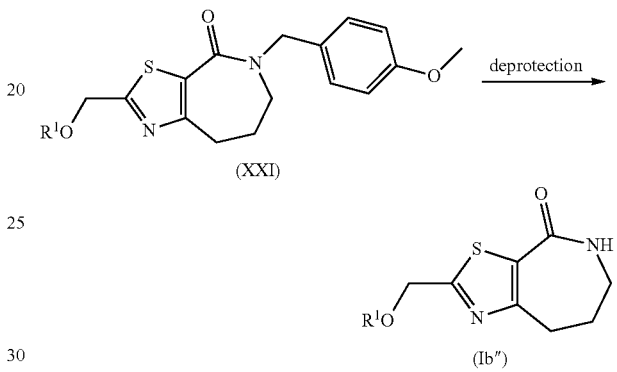

(XXI)

(Ib")

Experimental Procedure 19

Compounds according to Formula (XXI) can be prepared by reaction of an intermediate of Formula (XXII) with an appropriate thioacetamide of Formula (VIII) according to Reaction Scheme (19). The reaction is performed in a reaction-inert solvent, such as for example ethanol, at a moderately high temperature, such as for example 80° C., for a period of time that allows completion of the reaction. In Reaction Scheme (19), all variables are as defined in Formula (I).

Reaction Scheme 19

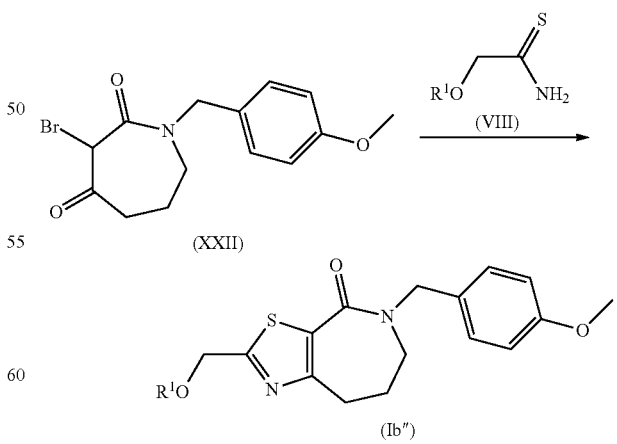

(XXII)

(Ib")

A compound of Formula (VIII) can be prepared according to the procedure described in WO 2007/056366 A2 (2007 May 18) or alternatively can be obtained commercially.

Experimental Procedure 20

The intermediate according to Formula (XXII) can be prepared by reaction of an intermediate of Formula (XXIII) with N-bromosuccinimide according to Reaction Scheme (20). The reaction is performed in a reaction-inert solvent, such as for example ethanol, in the presence of a suitable acid, such as for example sodium bisulfate hydrate at room temperature, for a period of time that allows completion of the reaction.

Reaction Scheme 20

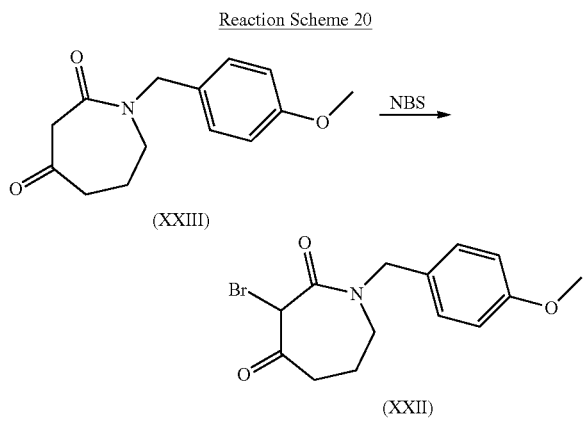

A compound of Formula (XXIII) can be prepared according to the procedure described in Synthesis, 2006, 14, 2319-2322.

Pharmacology

The compounds provided in this invention are positive allosteric modulators of metabotropic glutamate receptors, in particular they are positive allosteric modulators of mGluR5. The compounds of the present invention do not appear to bind to the glutamate recognition site, the orthosteric ligand site, but instead to an allosteric site. In the presence of glutamate or an agonist of mGluR5, the compounds of this invention increase the mGluR5 response. The compounds provided in this invention are expected to have their effect at mGluR5 by virtue of their ability to increase the response of such receptors to glutamate or mGluR5 agonists, enhancing the response of the receptor.

As used herein, the term "treatment" is intended to refer to all processes, wherein there may be a slowing, interrupting, arresting or stopping of the progression of a disease, but does not necessarily indicate a total elimination of all symptoms.

Hence, the present invention relates to a compound according to the present invention the stereoisomeric forms thereof and the pharmaceutically acceptable acid or base addition salts and the solvates thereof, for use as a medicine or for use as a medicament.

The invention also relates to the use of a compound according to the general Formula (I), the stereoisomeric forms thereof and the pharmaceutically acceptable acid or base addition salts and the solvates thereof, or a pharmaceutical composition according to the invention for the manufacture of a medicament, as well as to the use of a compound according to the invention or a pharmaceutical composition according to the invention for the manufacture of a medicament for treating or preventing, in particular treating, a condition in a mammal, including a human, the treatment or prevention of which is affected or facilitated by the neuromodulatory effect of allosteric modulators of mGluR5, in particular positive allosteric modulators thereof.

The invention also relates to a compound according to the general Formula (I), the stereoisomeric forms thereof and the pharmaceutically acceptable acid or base addition salts and the solvates thereof, or a pharmaceutical composition according to the invention for use in the treatment or prevention of, in particular treatment of, a condition in a mammal, including a human, the treatment or prevention of which is affected or facilitated by the neuromodulatory effect of allosteric modulators of mGluR5, in particular positive allosteric modulators thereof.

The present invention also relates to a compound according to the general Formula (I), the stereoisomeric forms thereof and the pharmaceutically acceptable acid or base addition salts and the solvates thereof, or a pharmaceutical composition according to the invention for use in the treatment, prevention, amelioration, control or reduction of the risk of various neurological and psychiatric disorders associated with glutamate dysfunction in a mammal, including a human, the treatment or prevention of which is affected or facilitated by the neuromodulatory effect of positive allosteric modulators of mGluR5.

Also, the present invention relates to the use of a compound according to the general Formula (I), the stereoisomeric forms thereof and the pharmaceutically acceptable acid or base addition salts and the solvates thereof, or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of positive allosteric modulators of mGluR5.

The present invention also relates to a compound according to the present invention or a pharmaceutical composition according to the invention for use in the manufacture of a medicament for treating or preventing, in particular treating, a condition in a mammal, including a human, the treatment or prevention of which is affected or facilitated by the neuromodulatory effect of allosteric modulators of mGluR5, in particular positive allosteric modulators thereof. The present invention also relates to a compound according to the present invention or a pharmaceutical composition according to the invention for treating or preventing, in particular treating, a condition in a mammal, including a human, the treatment or prevention of which is affected or facilitated by the neuromodulatory effect of allosteric modulators of mGluR5, in particular positive allosteric modulators thereof.

Also, the present invention relates to the use of a compound according to the invention or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of positive allosteric modulators of mGluR5.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such e.g. treatment, an effective amount of a compound or composition according to the invention.

In particular, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia (including positive, negative and cognitive symptoms thereof), anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

Preferably, the central nervous system disorder is a psychotic disorder selected from the group of schizophrenia, delusional disorder, schizoaffective disorder, schizophreniform disorder and substance-induced psychotic disorder Preferably, the central nervous system disorder is a personality disorder selected from the group of obsessive-compulsive personality disorder and schizoid, schizotypal disorder.

Preferably, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the central nervous system disorder is an eating disorder selected from the group of anorexia nervosa and bulimia nervosa.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is migraine.

Preferably, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Of the disorders mentioned above, the treatment of schizophrenia and dementia are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a compound according to the general Formula (I), the stereoisomeric forms thereof and the pharmaceutically acceptable acid or base addition salts and the solvates thereof, for use in the treatment of any one of the diseases mentioned hereinbefore.

The invention also relates to a compound according to the general Formula (I), the stereoisomeric forms thereof and the pharmaceutically acceptable acid or base addition salts and the solvates thereof, for use in treating any one of the diseases mentioned hereinbefore.

The invention also relates to a compound according to the general Formula (I), the stereoisomeric forms thereof and the pharmaceutically acceptable acid or base addition salts and the solvates thereof, for the treatment or prevention, in particular treatment, of any one of the diseases mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound of Formula (I), a stereoisomeric form thereof and a pharmaceutically acceptable addition salt or solvate thereof, to warm-blooded animals, including humans.

Therefore, the invention also relates to a method for the prevention and/or treatment of any one of the diseases mentioned hereinbefore comprising administering a therapeutically effective amount of a compound according to the invention to a patient in need thereof.

One skilled in the art will recognize that a therapeutically effective amount of the PAMs of the present invention is the amount sufficient to modulate the activity of the mGluR5 and that this amount varies inter alia, depending on the type of disease, the concentration of the compound in the therapeutic formulation, and the condition of the patient. Generally, an amount of PAM to be administered as a therapeutic agent for treating diseases in which modulation of the mGluR5 is beneficial, such as the disorders described herein, will be determined on a case by case by an attending physician.

Generally, a suitable dose is one that results in a concentration of the PAM at the treatment site in the range of 0.5 nM to 200 µM, and more usually 5 nM to 50 µM. To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Because such positive allosteric modulators of mGluR5, including compounds of Formula (I), enhance the response of mGluR5 to glutamate, it is an advantage that the present methods utilize endogenous glutamate.

Because positive allosteric modulators of mGluR5, including compounds of Formula (I), enhance the response of mGluR5 to agonists, it is understood that the present invention extends to the treatment of neurological and psychiatric disorders associated with glutamate dysfunction, such as for example those mentioned hereinbefore, by administering an effective amount of a positive allosteric modulator of mGluR5, including compounds of Formula (I), in combination with an mGluR5 agonist.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

Pharmaceutical Compositions

The present invention also provides compositions for preventing or treating diseases in which modulation of the mGluR5 receptor is beneficial, such as the disorders described herein. While it is possible for the active ingredient to be administered alone, it is preferable to present it as a pharmaceutical composition. Accordingly, the invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, an effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example surfactants, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs in the treatment, prevention, control, amelioration, or reduction of risk of diseases or conditions for which compounds of Formula (I) or the other drugs may have utility as well as to the use of such a composition for the manufacture of a medicament. The use of such a composition for the manufacture of a medicament in the treatment, prevention, control, amelioration or reduction of risk of diseases or conditions for which compounds of Formula (I) or the other drugs may have utility is also contemplated. The present invention also relates to a combination of a compound according to the present invention and a mGluR5 orthosteric agonist. The present invention also relates to such a combination for use as a medicine. The present invention also relates to a product comprising (a) a compound according to the present invention, a pharmaceutically acceptable salt thereof or a solvate thereof, and (b) a mGluR5 orthosteric agonist, as a combined preparation for simultaneous, separate or sequential use in the treatment or prevention of a condition in a mammal, including a human, such as for example a condition mentioned hereinbefore, the treatment or prevention of which is affected or facilitated by the neuromodulatory effect of mGluR5 allosteric modulators, in particular positive mGluR5 allosteric modulators. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Experimental Part

Several methods for preparing the compounds of this invention are illustrated in the following Examples. Unless otherwise noted, all starting materials were obtained from commercial suppliers and used without further purification.

Hereinafter, the term 'THF' means tetrahydrofuran, 'DMF' means N,N-dimethylformamide, 'DCM' means dichloromethane, 'ACN' means acetonitrile, 'AcOEt' means ethylacetate, 'AcOH' means acetic acid, 'EtOH' means ethanol, 'MeOH' means methanol, 'RP' means reverse phase.

Microwave assisted reactions were performed in a single-mode reactor: Initiator™ Sixty EXP microwave reactor (Biotage AB), or in a multimode reactor: MicroSYNTH Labstation (Milestone, Inc.).

Thin layer chromatography (TLC) was carried out on silica gel 60 F254 plates (Merck) using reagent grade solvents. Automated flash column chromatography was performed using ready-to-connect cartridges from Merck, on irregular silica gel, particle size 15-40 μm (normal phase disposable flash columns) on a SPOT or LAFLASH system from Armen Instrument. Isolute® SCX2 is a cartridge with silica-based sorbent with a chemically bonded propylsulfonic acid functional group.

A. Preparation of the Intermediates Example A1

Preparation of Intermediate 1

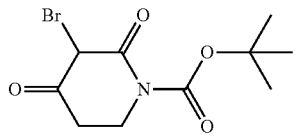 [SMILES: CC(C)(C)OC(=O)N1CCC(=O)C(Br)C1=O]

To a mixture of 2,4-dioxo-piperidine-1-carboxylic acid tert-butyl ester (40 g, 187.58 mmol) in carbon tetrachloride (500 mL) was added N-bromosuccinimide (33.38 g, 187.58 mmol) portionwise keeping the reaction temperature in the range of 10° C.-15° C. The mixture was further stirred at 10° C.-15° C. for 2 hours. The reaction mixture was allowed to warm to room temperature and the solvents evaporated in vacuo. The residue thus obtained was dissolved in AcOEt and washed with $H_2O$. The organic layer was separated, dried ($Na_2SO_4$), filtered and the solvents evaporated in vacuo to yield 30 g (55%) of racemic intermediate 1 that was used in the next step without further purification.

Example A2

Preparation of Intermediate 2

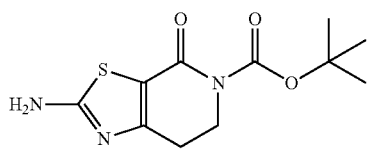 [SMILES: CC(C)(C)OC(=O)N1CCc2nc(N)sc2C1=O]

A mixture of intermediate 1 (25 g, 85.6 mmol), thiourea (6.5 g, 85.6 mmol) and $NaHCO_3$ (7.2 g, 85.6 mmol) in EtOH (400 mL) was heated at 80° C. for 2.5 hours. The reaction mixture was then cooled to room temperature and the solids were filtered off. The filtrate was evaporated in vacuo to give a residue that was crystallized from EtOH. The yellow crystals thus obtained were filtered off and dried to yield 15 g (66%) of intermediate 2.

Example A3

Preparation of Intermediate 3

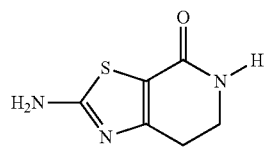 [SMILES: Nc1nc2c(s1)C(=O)NCC2]

A solution of intermediate 2 (15 g, 55.6 mmol) in a 4M solution of HCl in 1,4-dioxane (100 mL) was stirred at room temperature for 30 minutes. The solvent was evaporated in vacuo to yield 10 g (95%) of intermediate 3 as a yellow powder which was used in the next step without further purification.

Example A4

Preparation of Intermediate 4

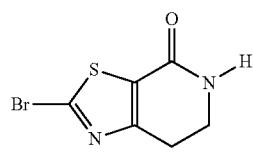

A mixture of intermediate 3 (8 g, 39.8 mmol), copper (II) bromide (10.43 g, 46.68 mmol) and 3-methyl-1-nitrosooxy-butane (6.8 g, 58.35 mmol) in ACN (100 mL) was stirred at room temperature for 1.5 hours. The solvent was evaporated in vacuo. The residue thus obtained was dissolved in AcOEt and washed with $H_2O$. The organic layer was separated, dried ($Na_2SO_4$), filtered and the solvents evaporated in vacuo to yield 5 g (55%) of intermediate 4 that was used in the next step without further purification.

Example A5

Preparation of Intermediate 5

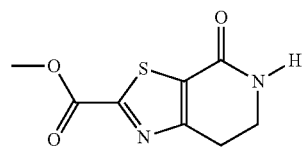

A mixture of triethylamine (17.2 g, 170 mmol) and 1,1'-bis(diphenylphosphino)ferrocenedichloro palladium (II) (2.0 g, 2.7 mmol) in THF (300 mL) was added to a solution of intermediate 4 (7.5 g, 23.6 mmol) in MeOH (300 mL). The mixture was stirred at 50° C. overnight under CO atmosphere (2.5 MPa). The reaction mixture was cooled, filtered and the solvent evaporated in vacuo. The crude product was purified by flash column chromatography (silica; DCM in MeOH 100/1). The desired fractions were collected and the solvents evaporated in vacuo to yield a yellow solid that was crystallized from AcOEt to yield 4.5 g (21%) of intermediate 5.

Example A6

Preparation of Intermediate 6

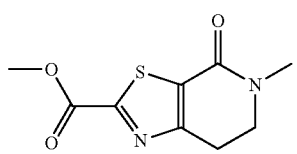

Iodomethane (4.4 mL, 70.68 mmol) was added to a suspension of intermediate 5 (10 g, 47.12 mmol) and $Cs_2CO_3$ (23 g, 70.68 mmol) in DMF (118 mL) and the mixture stirred at room temperature for 60 hours under nitrogen. The reaction mixture was diluted with $H_2O$ and extracted with AcOEt. The organic layer was separated, dried ($Na_2SO_4$), filtered and the solvents evaporated in vacuo. The crude product was purified by flash column chromatography (silica; AcOEt in DCM 0/100 to 50/50). The desired fractions were collected and the solvents evaporated in vacuo to yield intermediate 6 (4.46 g, 42%) as a pale brown oily solid.

Example A7

Preparation of Intermediate 7

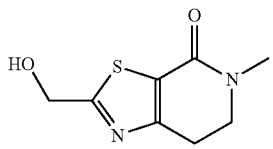

Sodium borohydride (0.15 g, 4.0 mmol) was added to a stirred solution of intermediate 6 (0.65 g, 2.87 mmol) in THF (8.8 mL) and MeOH (8.8 mL). The mixture was stirred at 0° C. for 30 minutes in a sealed tube under nitrogen and then diluted with $H_2O$ and extracted with DCM. The organic layer was separated, dried ($Na_2SO_4$), filtered and the solvents evaporated in vacuo. The aqueous phase was acidified with a 3N solution of HCl and extracted with DCM. The two organic layers were combined, dried ($Na_2SO_4$), filtered and the solvents evaporated in vacuo. The crude product was purified by flash column chromatography (silica; MeOH in AcOEt 0/100 to 20/80). The desired fractions were collected and the solvents evaporated in vacuo to yield intermediate 7 (0.59 g, 99%) as a dark oil.

Example A8

Preparation of Intermediate 8

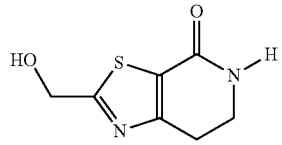 [SMILES: O=C1NCCc2nc(CO)sc21]

Intermediate 8 was prepared according to the synthetic procedure described in example A7, from intermediate 5.

Example A9

Preparation of Intermediate 9

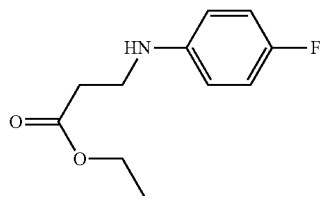

To a solution of 4-fluoroaniline (11.5 mL, 121.4 mmol) in AcOH (7 mL) was added ethyl acrylate (15.85 mL, 145.68 mmol). The mixture was stirred at 90° C. for 18 hours in a sealed tube. The reaction mixture was allowed to warm to room temperature and then was poured onto cooled water, basified by a 10% solution of $Na_2CO_3$ addition and extracted with DCM. The organic layer was separated, dried ($Na_2SO_4$), filtered and the solvents evaporated in vacuo. The residue was purified by flash column chromatography (silica; AcOEt in heptane 0/100 to 10/90). The desired fractions were collected and the solvents evaporated in vacuo to yield 24.6 g (66%) of intermediate 9.

Example A10

Preparation of Intermediate 10

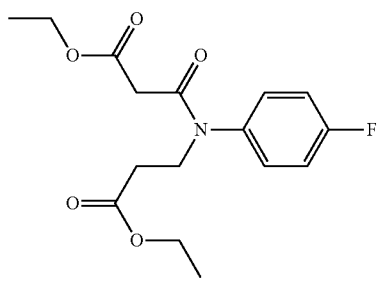 [SMILES: CCOC(=O)CCN(C(=O)CC(=O)OCC)c1ccc(F)cc1]

To a solution of intermediate 9 (10 g, 47.34 mmol) in DCM (10 mL), ethyl malonyl chloride (7.88 mL, 61.54 mmol) and N,N-diisopropylethylamine (16.49 mL, 94.68 mmol) were added. The mixture was stirred at room temperature for 1 hour and then diluted with further DCM and washed with a saturated solution of NH$_4$Cl. The organic layer was separated, dried (Na$_2$SO$_4$), filtered and the solvent evaporated in vacuo. The crude product was purified by flash column chromatography (silica; AcOEt in heptane 0/100 to 20/80). The desired fractions were collected and the solvents evaporated in vacuo to yield 11 g (71%) of intermediate 10 as an orange oil.

Example A11

Preparation of Intermediate 11

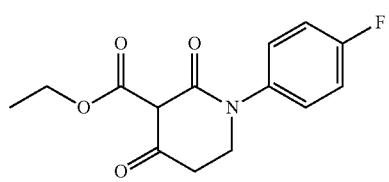 [SMILES: CCOC(=O)C1C(=O)CCN(c2ccc(F)cc2)C1=O]

A mixture of intermediate 10 (6.27 g, 19.27 mmol) in a 21% solution of sodium ethoxide in EtOH (14.39 mL, 38.55 mmol) was stirred at 85° C. for 16 hours. The solvent was evaporated in vacuo and the residue was partitioned between AcOEt and H$_2$O. The aqueous layer was separated, acidified by 1 N HCl solution addition and extracted with DCM. The organic layer was separated, dried (Na$_2$SO$_4$), filtered and the solvent evaporated in vacuo to yield 5 g (93%) of intermediate 11 used in next step without any further purification.

Example A12

Preparation of Intermediate 12

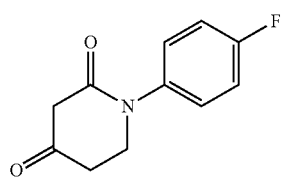 [SMILES: O=C1CCN(c2ccc(F)cc2)C(=O)C1]

A solution of intermediate 11 (7.5 g, 26.86 mmol) in a mixture of AcOH (0.6 mL) and H$_2$O (59.4 mL) was stirred at 90° C. for 16 hours. The reaction mixture was dried (MgSO$_4$), filtered and the solvents evaporated in vacuo to yield 5.5 g (99%) of intermediate 12 which was used in next step without any further purification.

Example A13

Preparation of Intermediate 13

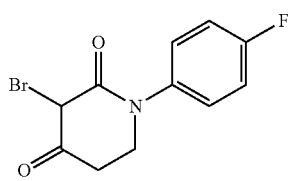 [SMILES: O=C1CCN(c2ccc(F)cc2)C(=O)C1Br]

To a solution of intermediate 12 (5.5 g, 26.54 mmol) in DCM (60 mL) at 0° C., N-bromosuccinimide (5.2 g, 29.2 mmol) was added. The mixture was stirred at 0° C. for 30 minutes and the solvent evaporated in vacuo to yield 7.7 g (>100%) of intermediate 13 used in next step without any further purification.

The following intermediates were prepared according to the synthetic procedures described in examples A9-A13

Example A14

Preparation of Intermediate 14

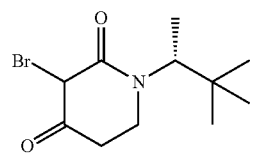

From (R)-(−)-3,3-dimethyl-2-butylamine and ethyl acrylate.

Example A15

Preparation of Intermediate 15

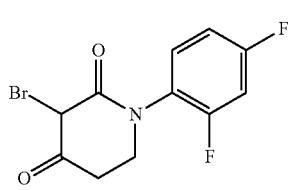 [SMILES: O=C1CCN(c2ccc(F)cc2F)C(=O)C1Br]

From 2,4-fluoroaniline and ethyl acrylate.

Example A16

Preparation of Intermediate 16

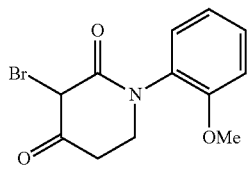 [SMILES: COc1ccccc1N1CCC(=O)C(Br)C1=O]

From 2-methoxyaniline and ethyl acrylate.

Example A17

Preparation of Intermediate 17

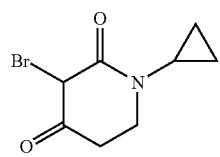 [SMILES: O=C1CCN(C2CC2)C(=O)C1Br]

From cyclopropylamine and ethyl acrylate.

Example A18

Preparation of Intermediate 18

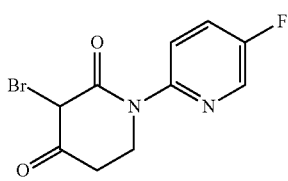

From 2-amino-5-fluoropyridine and ethyl acrylate.

Example A19

Preparation of Intermediate 19

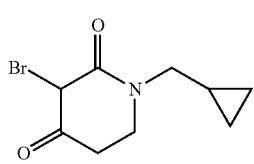

From cyclopropylethylamine and ethyl acrylate

Example A20

Preparation of Intermediate 20

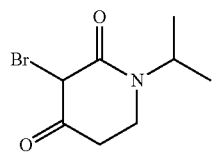

From isopropylamine and ethyl acrylate

Example A21

Preparation of Intermediate 21

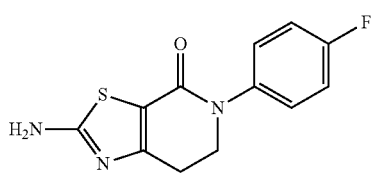 [SMILES: Nc1nc2c(s1)C(=O)N(c1ccc(F)cc1)CC2]

A mixture of intermediate 13 (4.14 g, 14.48 mmol), thiourea (1.1 g, 14.48 mmol) and NaHCO$_3$ (1.22 g, 14.48 mmol) in EtOH (60 mL) was heated at 80° C. for 1 hour. The reaction mixture was then cooled to room temperature and the solids were filtered off. The filtrate was evaporated in vacuo to yield 3.1 g (81%) of intermediate 21 used in next step without any further purification.

Example A22

Preparation of Intermediate 22

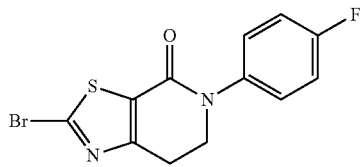 [SMILES: O=C1c2sc(Br)nc2CCN1c1ccc(F)cc1]

A mixture of intermediate 21 (3 g, 11.39 mmol), copper (II) bromide (3.05 g, 13.67 mmol) and 3-methyl-1-nitrosooxy-butane (2.3 mL, 17.09 mmol) in ACN (80 mL) was stirred at room temperature for 45 minutes. The reaction mixture was then concentrated in vacuo. The residue thus obtained was partitioned between AcOEt and H$_2$O. The organic layer was separated, dried (Na$_2$SO$_4$), filtered and the solvent evaporated in vacuo. The residue was purified by flash column chromatography (silica; AcOEt in heptane 0/100 to 30/70). The desired fractions were collected and the solvents evaporated in vacuo to yield 1.2 g (32%) of intermediate 22 as a white solid.

Example A23

Preparation of Intermediate 23

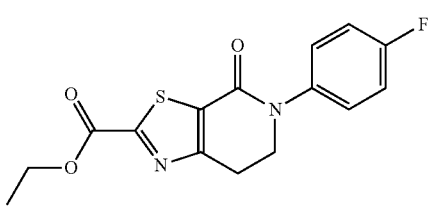 [SMILES: CCOC(=O)c1nc2c(s1)C(=O)N(c1ccc(F)cc1)CC2]

A mixture of intermediate 13 (11.8 g, 41.3 mmol), ethyl thiooxamate (5.5 g, 41.3 mmol) and NaHCO$_3$ (8.7 g, 82 mmol) in EtOH (400 mL) was stirred at 80° C. for 2 hours. The reaction mixture was cooled, filtered and the solvent evaporated in vacuo. The crude product was purified by flash column chromatography (silica; AcOEt in petroleum ether 10/1 to 2/1). The desired fractions were collected and the solvents evaporated in vacuo to yield 2 g (15%) of intermediate 23.

Example A24

Preparation of Intermediate 24

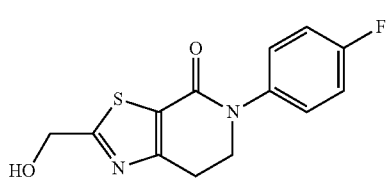 [SMILES: O=C1c2sc(CO)nc2CCN1c1ccc(F)cc1]

Sodium borohydride (0.7 g, 18.7 mmol) was added to a solution of intermediate 23 (2 g, 6.3 mmol) in MeOH (50 mL) at 0° C. The reaction mixture was stirred at room temperature for 2 hours, quenched with H$_2$O and extracted with AcOEt. The organic layer was separated, dried (Na$_2$SO$_4$), filtered and the solvents evaporated in vacuo. The crude product was purified by flash column chromatography (silica; AcOEt in petroleum ether 4/1 to 1/2). The desired fractions were collected and the solvents evaporated in vacuo to yield 1 g (53%) of intermediate 24 as a solid.

The following intermediate was prepared according to the synthetic procedure described in example A21-A24:

Example A25

Preparation of Intermediate 25

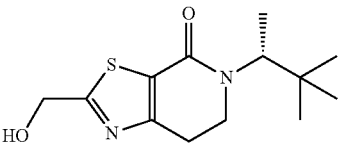 [SMILES: C[C@@H](N1CCc2nc(CO)sc2C1=O)C(C)(C)C]

From intermediate 14.

Example A26

Preparation of Intermediate 26

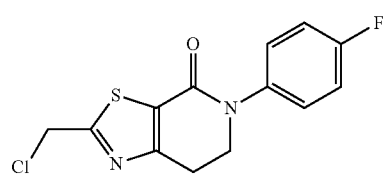 [SMILES: O=C1c2sc(CCl)nc2CCN1c1ccc(F)cc1]

Intermediate 24 (1 g, 3.6 mmol) was added to a mixture of thionyl chloride (10 mL) and DCM (10 mL). The mixture was stirred at room temperature for 2 hours and the solvents evaporated in vacuo to yield 1 g (100%) of intermediate 26 that was used in the next step without further purification.

The following intermediate was prepared according to the synthetic procedure described in example A26

Example A27

Preparation of Intermediate 27

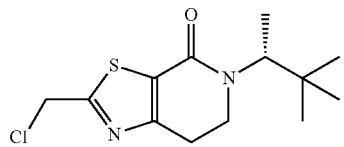 [SMILES: C[C@@H](N1CCc2nc(CCl)sc2C1=O)C(C)(C)C]

From intermediate A25.

The following intermediates were prepared according to the synthetic procedures described in examples A21-A24, A26

Example A28

Preparation of Intermediate 28

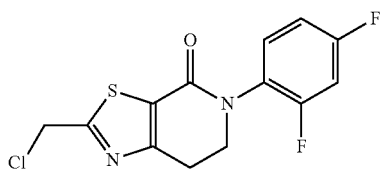 [SMILES: O=C1c2sc(CCl)nc2CCN1c1ccc(F)cc1F]

From intermediate 15.

Example A29

Preparation of Intermediate 29

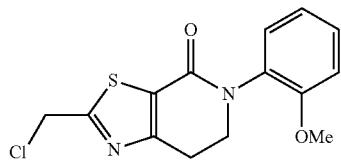 [SMILES: COc1ccccc1N1CCc2nc(CCl)sc2C1=O]

From intermediate 16.

Example A30

Preparation of Intermediate 30

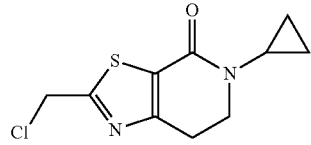 [SMILES: O=C1c2sc(CCl)nc2CCN1C1CC1]

From intermediate 17.

Example A31

Preparation of Intermediate 31

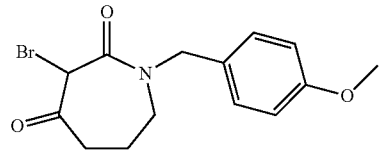 [SMILES: COc1ccc(CN2CCCC(=O)C(Br)C2=O)cc1]

N-Bromosuccinimide (2.88 g, 16.17 mmol) was added portionwise to a stirred solution of 1-(4-methoxy-benzyl)-azepane-2,4-dione (prepared according to the procedure described in Synthesis, 2006, 14, 2319-2322, 4.0 g, 16.17 mmol) and NaHSO$_4$H$_2$O (0.67 g, 4.85 mmol) in THF anhydrous (80 mL) at 0° C. The reaction mixture was stirred at room temperature for 2.5 hours and the solvent evaporated in vacuo to yield 8 g (91%, 60% pure) of intermediate 31 as a viscous orange oil which was used in the next step without further purification.

Example A32

Preparation of Intermediate 32

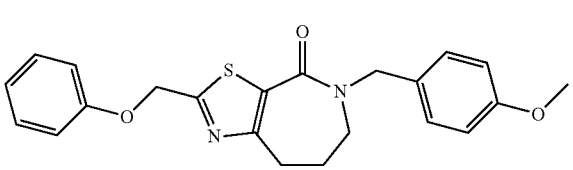 [SMILES: COc1ccc(CN2CCCc3nc(COc4ccccc4)sc3C2=O)cc1]

A mixture of intermediate 31 (0.78 g, 2.38 mmol) and 2-phenoxythioacetamide (0.36 g, 2.14 mmol) in DMF (12.5 mL) was stirred at room temperature for 15 minutes. Then NaHCO$_3$ (0.32 g, 3.81 mmol) was added and the reaction was stirred at 100° C. for 30 minutes. The reaction was diluted with H$_2$O and extracted with AcOEt. The organic layer was separated, dried (Na$_2$SO$_4$), filtered and the solvents evaporated in vacuo. The crude product was purified by flash column chromatography (silica; DCM in heptane 0/100 to 100/0). The desired fractions were collected and the solvents evaporated in vacuo to yield 58 g (62%) of intermediate 32 as an orange oil.

B. Preparation of the Final Compounds

Example B1

Preparation of Compound 1

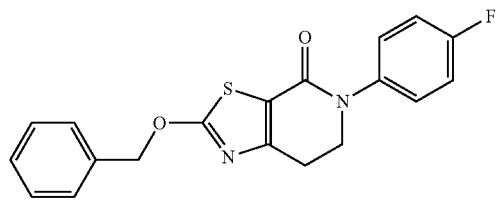 [SMILES: O=C1c2sc(OCc3ccccc3)nc2CCN1c1ccc(F)cc1]

Benzyl alcohol (0.38 mL, 3.67 mmol) was added dropwise to a 60% dispersion of sodium hydride in mineral oils (0.183 g, 4.58 mmol) in THF (12 mL), under a nitrogen atmosphere. The mixture was stirred at room temperature for 15 minutes and then intermediate 22 (1 g, 3.06 mmol) was added. The mixture was stirred at 120° C. for 25 minutes in a sealed tube under microwave irradiation. The mixture was partitioned between DCM and H$_2$O. The organic layer was separated, dried (MgSO$_4$), filtered and the solvent evaporated in vacuo. The crude product was purified by flash column chromatography (silica; AcOEt in DCM in heptane 0/0/100 to 10, 10, 1980). The desired fractions were collected and evaporated in vacuo to yield 0.68 g (63%) of compound 1 as a white solid. C$_{19}$H$_{15}$FN$_2$O$_2$S $^1$H NMR (400 MHz, CDCl$_3$) δ ppm 3.08 (t, J=6.9 Hz, 2H), 4.01 (t, J=6.9 Hz, 2H), 5.49 (s, 2H), 7.08 (t, J=8.7 Hz, 2H), 7.29 (dd, J=9.0, 4.9 Hz, 2H), 7.34-7.54 (m, 5H).

Example B2

Preparation of Compound 2

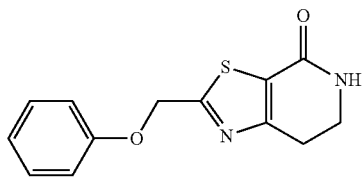 [SMILES: O=C1NCCc2nc(COc3ccccc3)sc21]

Di-tert-butyl azodicarboxylate (3.0 g, 13.0 mmol) was added to a stirred solution of intermediate 8 (2.0 g, 10.8 mmol), phenol (1.20 g, 13.0 mmol) and triphenylphosphine (3.4 g, 13.0 mmol) in THF (31 mL) in a sealed tube and under nitrogen. The mixture was stirred at 120° C. for 20 minutes under microwave irradiation and then the solvent evaporated in vacuo. The crude product was purified by flash column chromatography (silica; 7M solution of ammonia in methanol in DCM 0/100 to 5/95). The desired fractions were collected and the solvents evaporated in vacuo to yield (1.82 g, 64% yield, 69% pure). Part of the product (0.14 g) was repurified by HPLC (gradient elution: 0.1% TFA in ACN/0.1% TFA in H$_2$O). The desired fractions were collected and the solvents evaporated in vacuo to yield compound 2 (51 mg) as a white solid. C$_{13}$H$_{12}$N$_2$O$_2$S $^1$H NMR (400 MHz, CDCl$_3$) δ ppm 3.12 (t, J=7.1 Hz, 2H), 3.69 (td, J=7.1, 2.8 Hz, 2H), 5.35 (s, 2H), 5.96 (br. s., 1H), 6.96-7.07 (m, 3H), 7.28-7.43 (m, 2H)

Example B3

Preparation of Compound 3

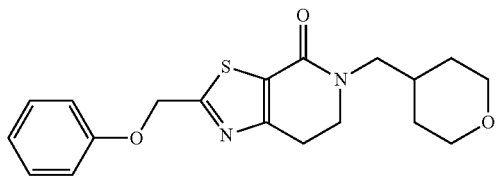 [SMILES: O=C1c2sc(COc3ccccc3)nc2CCN1CC1CCOCC1]

A 60% dispersion of sodium hydride in mineral oils (0.034 g, 0.86 mmol) was added to a solution of compound 2 (0.15 g, 0.57 mmol) in DMF (2.5 mL) at 0° C. and the mixture stirred at room temperature for 1 hour. Then 4-(bromomethyl)tetrahydropyran (0.15 g, 0.57 mmol) was added and the mixture stirred at room temperature for 16 hours, diluted with H$_2$O and extracted with AcOEt. The organic layer was separated, dried (Na$_2$SO$_4$), filtered and the solvents evaporated in vacuo. The crude product was purified by flash column chromatography (silica; 7 M solution of ammonia in MeOH in DCM 0/100 to 4/96). The desired fractions were collected and the solvents evaporated in vacuo. The product obtained was triturated with DIPE and repurified by RP HPLC (80% 0.1% NH$_4$CO$_3$H/NH$_4$OH pH 9 solution in H$_2$O, 20% ACN to 0% 0.1% NH$_4$CO$_3$H/NH$_4$OH pH 9 solution in H$_2$O, 100% ACN) to yield compound 3 (0.027 g, 13% yield) as a white solid. C$_{19}$H$_{22}$N$_2$O$_3$S $^1$H NMR (400 MHz, CDCl$_3$) δ ppm 1.34-1.48 (m, 2H), 1.59-1.68 (m, 2H), 1.90-2.04 (m, 1H), 3.11 (t, J=7.0 Hz, 2H), 3.32-3.42 (m, 2H), 3.40 (d, J=7.4 Hz, 2H), 3.69 (t, J=7.0 Hz, 2H), 3.94-4.03 (m, 2H), 5.33 (s, 2H), 6.97-7.05 (m, 3H), 7.28-7.35 (m, 2H)

Example B4

Preparation of Compound 4

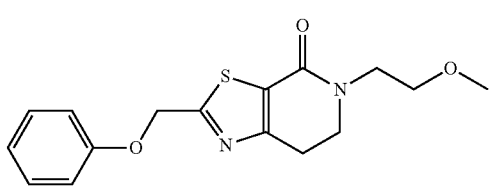 [SMILES: COCCN1CCc2nc(COc3ccccc3)sc2C1=O]

2-Bromoethylmethylether (0.081 mL, 0.86 mmol) was added to a suspension of compound 2 (0.15 g, 0.57 mmol) and Cs$_2$CO$_3$ (0.28 g, 0.86 mmol) in DMF (2.5 mL) and then the mixture was stirred at room temperature for 16 hours under nitrogen. The mixture was then stirred at 100° C. for 1 hour, diluted with H$_2$O and extracted with AcOEt. The organic layer was separated, washed with brine, dried (Na$_2$SO$_4$), filtered and the solvents evaporated in vacuo. The crude product was purified by flash column chromatography (silica; AcOEt in DCM 0/100 to 50/50). The desired fractions were collected and the solvents evaporated in vacuo. The product was triturated with DIPE to yield compound 4 (0.09 g, 49% yield) as a yellow solid. C$_{16}$H$_{18}$N$_2$O$_3$S $^1$H NMR (500 MHz, CDCl$_3$) δ ppm 3.10 (t, J=7.1 Hz, 2H), 3.36 (s, 3H), 3.60 (t, J=5.2 Hz, 2H), 3.69 (t, J=5.2 Hz, 2H), 3.78 (t, J=7.2 Hz, 2H), 5.33 (s, 2H), 6.97-7.04 (m, 3H), 7.28-7.35 (m, 2H)

Example B5

Preparation of Compound 5

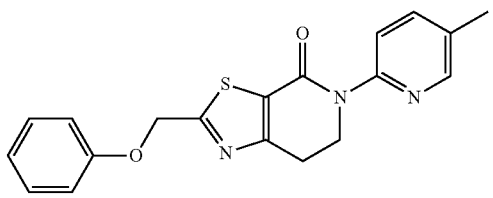 [SMILES: Cc1ccc(N2CCc3nc(COc4ccccc4)sc3C2=O)nc1]

K$_2$CO$_3$ (0.16 g, 1.15 mmol) was added to a stirred suspension of compound 2 (0.15 g, 0.57 mmol), 2-bromo-5-methylpyridine (0.10 g, 0.57 mmol), copper (I) iodide (0.022 g, 0.11 mmol) and N,N'-dimethylethylenediamine (0.037 mL, 0.34 mmol) in toluene (3 mL) in a sealed tube and under nitrogen. The mixture was stirred at 120° C. for 16 hours, filtered through a pad of diatomaceous earth, washed with AcOEt and the filtrate evaporated in vacuo. The crude product was purified by flash column chromatography (silica; AcOEt in DCM 0/100 to 100/0). The desired fractions were collected and the solvents evaporated in vacuo. The product was repurified by ion exchange chromatography using an Isolute® SCX2 cartridge eluting with 7 M ammonia solution in MeOH. The product was then repurified by flash column chromatography (silica; AcOEt in DCM 0/100 to 50/50). The desired fractions were collected and concentrated in vacuo.

The residue was purified by RP HPLC (Gradient from 80% 0.1% NH$_4$CO$_3$H/NH$_4$OH pH 9 solution in H$_2$O, 20% ACN to 0% 0.1% NH$_4$CO$_3$H/NH$_4$OH pH 9 solution in H$_2$O, 100% ACN) to yield compound 6 (16 mg, 8% yield) as a white solid. C$_{19}$H$_{17}$N$_3$O$_2$S $^1$H NMR (400 MHz, CDCl$_3$) δ ppm 2.33 (s, 3H), 3.22 (t, J=6.8 Hz, 2H), 4.42 (t, J=6.8 Hz, 2H), 5.37 (s, 2H), 6.99-7.07 (m, 3H), 7.29-7.37 (m, 2H), 7.53 (ddd, J=8.3, 2.3, 0.5 Hz, 1H), 7.75 (d, J=8.3 Hz, 1H), 8.23-8.27 (m, 1H)

Example B6

Preparation of Compound 6

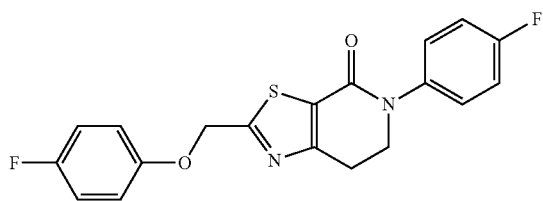 [SMILES: O=C1c2sc(COc3ccc(F)cc3)nc2CCN1c1ccc(F)cc1]

4-Fluorophenol (0.15 g, 1.30 mmol) was added to a stirred solution of intermediate 26 (0.33 g, 1.34 mmol) and K$_2$CO$_3$ (0.41 g, 3.0 mmol) in DMF (40 mL). The reaction mixture was stirred at room temperature for 1 day, filtered and the solvent evaporated in vacuo. The residue was purified by RP HPLC (gradient elution: 0.1% TFA in ACN/0.1% TFA in H$_2$O). The desired fractions were collected, washed with a saturated solution of NaHCO$_3$ and extracted with AcOEt. The combined organic layers were separated, dried (Na$_2$SO$_4$), filtered and the solvents evaporated in vacuo to yield compound 6 (74 mg, 20% yield) as a solid. C$_{19}$H$_{14}$F$_2$N$_2$O$_2$S $^1$H NMR (300 MHz, CDCl$_3$) δ ppm 3.25 (t, J=6.7 Hz, 2H), 4.07 (t, J=6.8 Hz, 2H), 5.31 (s, 2H), 6.85-7.05 (m, 4H), 7.09 (br. t, J=8.4, 8.4 Hz, 2H), 7.26-7.35 (m, 2H).

Example B7

Preparation of Compound 7

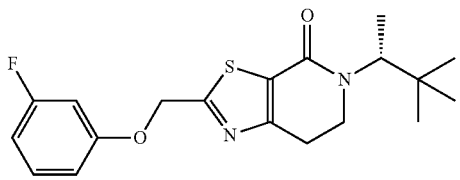 [SMILES: C[C@@H](N1CCc2nc(COc3cccc(F)c3)sc2C1=O)C(C)(C)C]

Di-ethyl-azodicarboxylate (0.4 g, 2.2 mmol) was added to a stirred solution of triphenylphosphine (0.54 g, 2.1 mmol) in THF (10 mL) under nitrogen. The mixture was stirred at room temperature for 10 minutes followed by the addition of intermediate 25 (0.3 g, 1.1 mmol) and 3-fluorophenol (0.3 g, 2.6 mmol), then the mixture was stirred at room temperature for 2 hours. The solvent was evaporated in vacuo and the crude product purified by flash column chromatography (silica; AcOEt in petroleum ether 1/15 to 1/10). The desired fractions were collected and the solvents evaporated in vacuo to yield compound 7 (0.065 g, 16% yield) as a white solid. C$_{19}$H$_{23}$FN$_2$O$_2$S $^1$H NMR (400 MHz, DMSO-d$_6$) δ ppm 0.90 (s, 9H), 1.15 (d, J=7.3 Hz, 3H), 2.92-3.08 (m, 2H), 3.58 (t, J=6.7 Hz, 2H), 4.48 (q, J=7.1 Hz, 1H), 5.48 (s, 2H), 6.84 (td, J=8.3, 1.8 Hz, 1H), 6.93 (dd, J=8.4, 1.9 Hz, 1H), 7.00 (dt, J=11.2, 1.8 Hz, 1H), 7.32-7.40 (m, 1H).

Example B8

Preparation of Compound 8

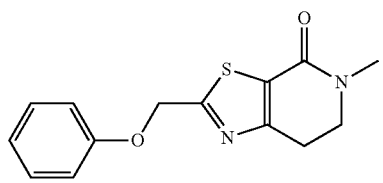 [SMILES: CN1CCc2nc(COc3ccccc3)sc2C1=O]

Di-tert-butyl-azodicarboxylate (0.48 g, 2.12 mmol) was added to a stirred solution of triphenylphosphine (0.55 g, 2.12 mmol), intermediate 7 (0.35 g, 1.76 mmol) and phenol (0.2 g, 2.12 mmol), in THF (7.2 mL) The mixture was stirred at 0° C. for 5 minutes and then at room temperature for 2 hours in a sealed tube under nitrogen. Then di-tert-butyl azodicarboxylate (0.20 g, 0.42 mmol), triphenylphosphine (0.23 g, 0.42 mmol), phenol (0.08 g, 0.42 mmol) were added again and the resulting mixture stirred at 0° C. for 5 minutes at room temperature for 1 hour. The solvent was evaporated in vacuo and the crude product purified by flash column chromatography (silica; AcOEt in DCM 0/100 to 40/60). The desired fractions were collected and the solvents evaporated in vacuo to afford a product that was triturated with DIPE to yield compound 8 (0.26 g, 53% yield) as a white solid. C$_{14}$H$_{14}$N$_2$O$_2$S $^1$H NMR (500 MHz, CDCl$_3$) δ ppm 3.10 (s, 3H), 3.14 (t, J=7.2 Hz, 2H), 3.67 (t, J=7.1 Hz, 2H), 5.33 (s, 2H), 6.96-7.05 (m, 3H), 7.28-7.35 (m, 2H).

Example B9

Preparation of Compound 9

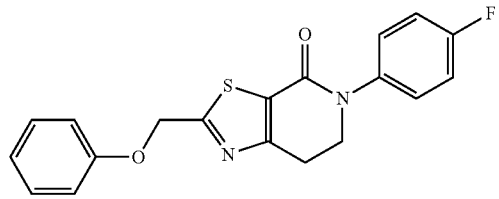

A mixture of intermediate 13 (0.41 g, 1.45 mmol) and 2-phenoxy-thioacetamide (0.22 g, 1.3 mmol) in DMF (5 mL) was stirred at room temperature for 15 minutes before NaHCO$_3$ (0.19 g, 2.3 mmol) was added. The mixture was stirred at 100° C. for 30 minutes, diluted with AcOEt and washed with H$_2$O. The organic layer was separated, dried (MgSO$_4$), filtered and the filtrate evaporated in vacuo. The product was purified by flash column chromatography (silica; AcOEt in DCM 100/0 to 98/2). The desired fractions were collected and evaporated in vacuo to yield compound 9 (0.084 g, 16% yield) as a white solid. C$_{19}$H$_{15}$FN$_2$O$_2$S $^1$H NMR (500

MHz, CDCl$_3$) δ ppm 3.26 (t, J=6.9 Hz, 2H), 4.08 (t, J=6.9 Hz, 2H), 5.36 (s, 2H), 6.98-7.06 (m, 3H), 7.07-7.13 (m, 2H), 7.28-7.36 (m, 4H)

Example B10

Preparation of Compound 10

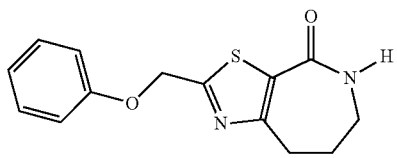 [SMILES: O=C1NCCCc2nc(COc3ccccc3)sc21]

A solution of ammonium cerium (IV) nitrate (1.08 g, 1.97 mmol) in H$_2$O (1.5 mL) was added to a stirred solution of intermediate 32 (0.22 g, 0.56 mmol) in ACN (5 mL). The mixture was stirred at room temperature for 16 hours and then diluted with H$_2$O and extracted with AcOEt. The organic layer was separated, dried (Na$_2$SO$_4$), filtered and the solvents evaporated in vacuo. The crude product was purified by flash column chromatography (silica; AcOEt in DCM 0/100 to 100/0). The desired fractions were collected and the solvents evaporated in vacuo to yield 0.081 g (52%) of compound 10 as a white solid. C$_{14}$H$_{14}$N$_2$O$_2$S $^1$H NMR (400 MHz, CDCl$_3$) δ ppm 2.12-2.22 (m, 2H), 3.21 (t, J=6.5 Hz, 2H), 3.42-3.47 (m, 2H), 5.27 (s, 2H), 6.50 (br. s., 1H), 6.96-7.04 (m, 3H), 7.27-7.35 (m, 2H)

Example B11

Preparation of Compound 11

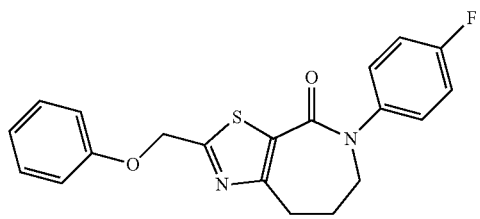 [SMILES: O=C1c2sc(COc3ccccc3)nc2CCCN1c1ccc(F)cc1]

K$_2$CO$_3$ (0.05 g, 0.36 mmol) was added to a stirred suspension of compound 10 (0.05 g, 0.18 mmol), 1-bromo-4-fluorobenzene (0.04 mL, 0.3 mmol), copper (I) iodide (0.007 g, 0.036 mmol) and N,N'-dimethylethylenediamine (0.017 mL, 0.11 mmol) in 1,4-dioxane (1 mL) in a sealed tube and under nitrogen. The mixture was stirred at 150° C. for 16 hours and then quenched with an aqueous saturated solution of NH$_4$Cl and extracted with AcOEt. The organic layer was separated, dried (Na$_2$SO$_4$), filtered and the solvents evaporated in vacuo. The crude product was purified by flash column chromatography (silica; AcOEt in DCM 0/100 to 20/80). The desired fractions were collected and the solvents evaporated in vacuo to yield compound 11 (34 mg, 50% yield) as a yellow solid. C$_{20}$H$_{17}$FN$_2$O$_2$S $^1$H NMR (400 MHz, CDCl$_3$) δ ppm 2.28-2.35 (m, 2H), 3.25 (t, J=6.9 Hz, 2H), 3.85-3.90 (m, 2H), 5.29 (s, 2H), 6.98-7.04 (m, 3H), 7.05-7.13 (m, 2H), 7.21-7.27 (m, 2H), 7.28-7.35 (m, 2H)

Table 1 lists the compounds that were prepared according to the above Examples.

TABLE 1

| Co. No. | Ex. No. | n | ----A—R$^1$ | ----R$^2$ | Salt data |
|---|---|---|---|---|---|
| 1 | B1 | 1 | phenyl-CH$_2$-O- | 4-fluorophenyl | |
| 2 | B2 | 1 | phenyl-O-CH$_2$- | ----H | |
| 3 | B3 | 1 | phenyl-O-CH$_2$- | tetrahydropyran-4-ylmethyl | |
| 4 | B4 | 1 | phenyl-O-CH$_2$- | 2-methoxyethyl | |
| 5 | B5 | 1 | phenyl-O-CH$_2$- | 5-methylpyridin-2-yl | |

TABLE 1-continued

| Co. No. | Ex. No. | n | ----A—R¹ | ----R² | Salt data |
|---|---|---|---|---|---|
| 6 | B6 | 1 | 4-F-phenyl-O-CH₂- | 4-F-phenyl | |
| 7 | B7 | 1 | 3-F-phenyl-O-CH₂- | (R)-CH(CH₃)-C(CH₃)₃ | |
| 8 | B8 | 1 | phenyl-O-CH₂- | -CH₃ | |
| 9 | B9 | 1 | phenyl-O-CH₂- | 4-F-phenyl | |
| 10 | B10 | 2 | phenyl-O-CH₂- | -H | |
| 11 | B11 | 2 | phenyl-O-CH₂- | 4-F-phenyl | |
| 12 | B1 | 1 | phenyl-CH₂-O- | 2,4-diF-phenyl | |
| 13 | B4 | 1 | phenyl-CH₂-O- | 2,4-diF-benzyl | |
| 14 | B4 | 1 | phenyl-CH₂-O- | 4-F-benzyl | |
| 15 | B4 | 1 | phenyl-CH₂-O- | 3-F-benzyl | |
| 16 | B4 | 1 | phenyl-CH₂-O- | 2-F-benzyl | |

TABLE 1-continued

| Co. No. | Ex. No. | n | ----A—R¹ | ----R² | Salt data |
|---|---|---|---|---|---|
| 17 | B1 | 1 | 3-fluorobenzyloxy | 2,4-difluorophenyl | |
| 18 | B1 | 1 | 2-fluorobenzyloxy | 2,4-difluorophenyl | |
| 19 | B1 | 1 | 3-fluorobenzyloxy | 4-fluorophenyl | |
| 20 | B1 | 1 | 3-cyanobenzyloxy | 2,4-difluorophenyl | |
| 21 | B1 | 1 | 3-methylbenzyloxy | 2,4-difluorophenyl | |
| 22 | B1 | 1 | 2-fluorobenzyloxy | 4-fluorophenyl | |
| 23 | B1 | 1 | 2,4-difluorobenzyloxy | 2,4-difluorophenyl | |
| 24 | B3 | 1 | benzyloxy | -CH₃ | |
| 25 | B9 | 1 | 3-fluorophenoxyethyl | 4-fluorophenyl | |
| 26 | B1 | 1 | 3-fluorobenzyloxy | 4-(trifluoromethyl)phenyl | |

TABLE 1-continued
| Co. No. | Ex. No. | n | ----A—R¹ | ----R² | Salt data |
|---|---|---|---|---|---|
| 27 | B1 | 1 | 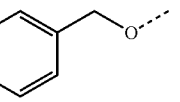 | 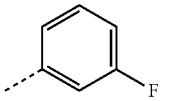 | |
| 28 | B9 | 1 | 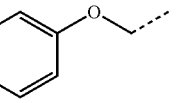 | 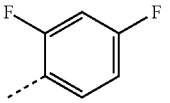 | |
| 29 | B9 | 1 | 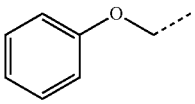 | 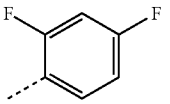 | |
| 30 | B1 | 1 | 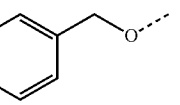 | 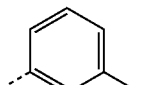 | |
| 31 | B6 | 1 | 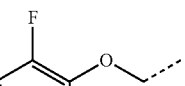 | 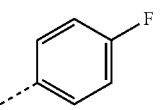 | |
| 32 | B6 | 1 | 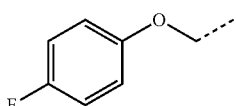 | 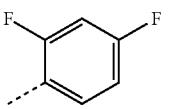 | |
| 33 | B6 | 1 | 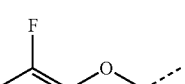 | 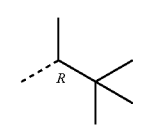 | |
| 34 | B6 | 1 | 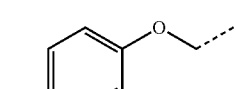 | 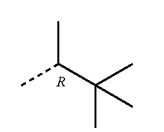 | |
| 35 | B6 | 1 | 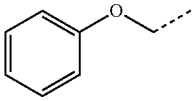 | 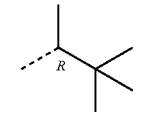 | |
| 36 | B6 | 1 | 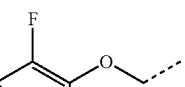 | 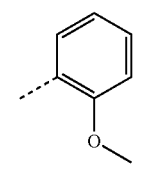 | |

TABLE 1-continued
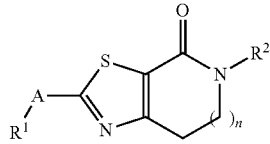
| Co. No. | Ex. No. | n | ----A—R¹ | ----R² | Salt data |
|---|---|---|---|---|---|
| 37 | B6 | 1 | 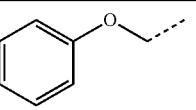 | 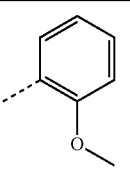 | |
| 38 | B3 | 2 | 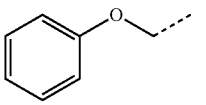 | ----CH₃ | |
| 39 | B9 | 1 |  | 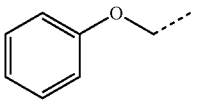 | |
| 40 | B6 | 1 |  | 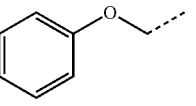 | |
| 41 | B9 | 1 |  | 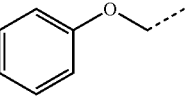 | |
| 42 | B9 | 1 |  | 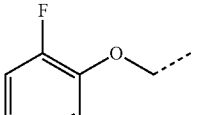 | |
| 43 | B9 | 1 | 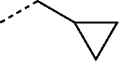 | 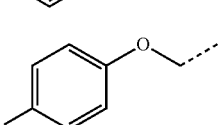 | |
| 44 | B6 | 1 | 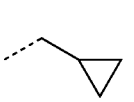 | 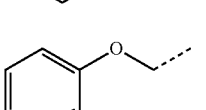 | |
| 45 | B5 | 1 |  | 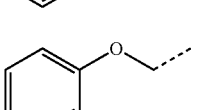 | |
| 46 | B5 | 1 | 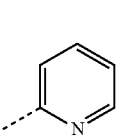 | 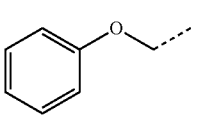 | |
| 47 | B5 | 1 | 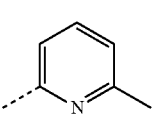 | 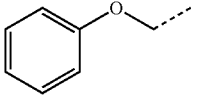 | |

TABLE 1-continued

| Co. No. | Ex. No. | n | ----A—R¹ | ----R² | Salt data |
|---|---|---|---|---|---|
| 48 | B5 | 1 | phenoxyethyl | pyridin-3-yl | |
| 49 | B5 | 1 | phenoxyethyl | pyridin-4-yl | |
| 50 | B5 | 1 | phenoxyethyl | 3-fluoropyridin-2-yl | |
| 51 | B5 | 1 | phenoxyethyl | 4-methylpyridin-2-yl | |
| 52 | B5 | 1 | phenoxyethyl | 3-methylpyridin-2-yl | |
| 53 | B9 | 1 | (4-fluorophenoxy)ethyl | 5-fluoropyridin-2-yl | |
| 54 | B9 | 1 | (3-fluorophenoxy)ethyl | 5-fluoropyridin-2-yl | |
| 55 | B9 | 1 | (2-fluorophenoxy)ethyl | 5-fluoropyridin-2-yl | |
| 56 | B4 | 1 | phenoxyethyl | propyl | |
| 57 | B5 | 1 | phenoxyethyl | 5-fluoropyridin-3-yl | |
| 58 | B5 | 1 | phenoxyethyl | 3,5-difluoropyridin-4-yl | |

TABLE 1-continued
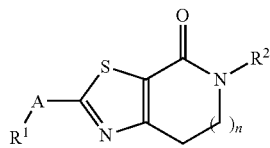
| Co. No. | Ex. No. | n | ----A—R¹ | ----R² | Salt data |
|---|---|---|---|---|---|
| 59 | B6 | 1 | 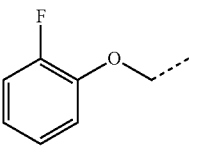 | 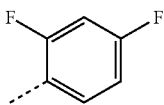 | |
| 60 | B9 | 1 | 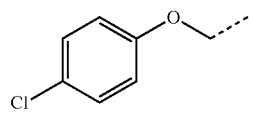 | 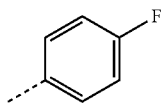 | |
| 61 | B6 | 1 | 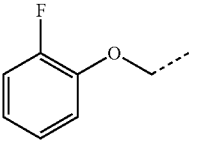 |  | |
| 62 | B6 | 1 | 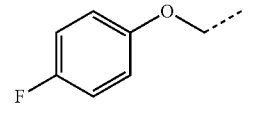 |  | |
| 63 | B9 | 1 | 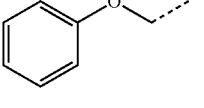 |  | |
| 64 | B9 | 1 | 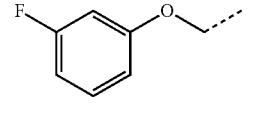 |  | |
| 65 | B1 | 1 | 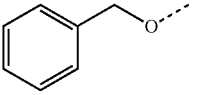 | ----H | |
| 66 | B1 | 1 |  | ----H | |
| 67 | B1 | 1 | 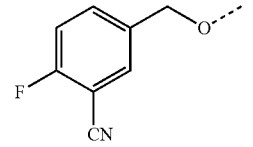 | ----H | |
| 68 | B1 | 1 |  | ----H | |

TABLE 1-continued
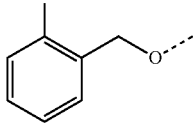
| Co. No. | Ex. No. | n | ----A—R¹ | ----R² | Salt data |
|---|---|---|---|---|---|
| 69 | B1 | 1 | 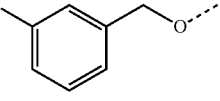 | ----H | Trifluoroacetate (•C₂HF₃O₂) |
| 70 | B1 | 1 | 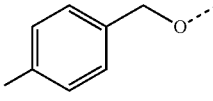 | ----H | Trifluoroacetate (•C₂HF₃O₂) |
| 71 | B1 | 1 | 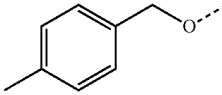 | ----H | Trifluoroacetate (•C₂HF₃O₂) |
| 72 | B1 | 1 | 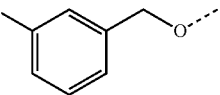 | ----H | |
| 73 | B1 | 1 | 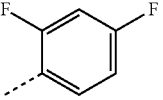 | 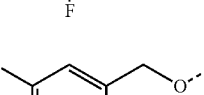 | |
| 74 | B1 | 1 | 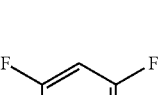 | 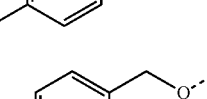 | |
| 75 | B1 | 1 | 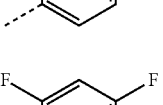 | 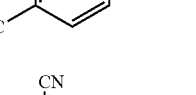 | |
| 76 | B1 | 1 | 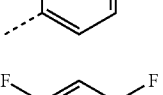 | 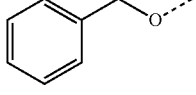 | |
| 77 | B1 | 1 | 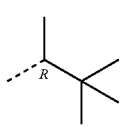 | 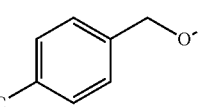 | |
| 78 | B1 | 1 | 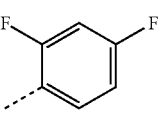 | | |

TABLE 1-continued

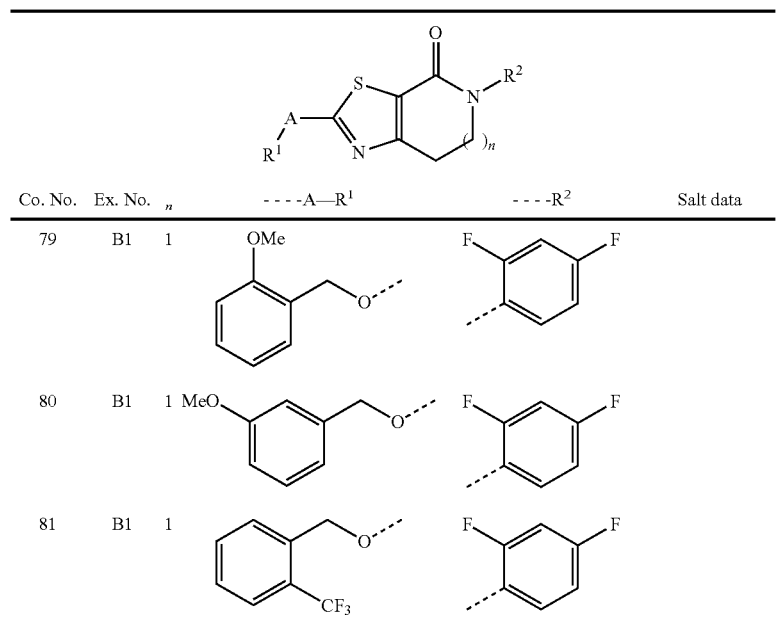

| Co. No. | Ex. No. | n | ----A—R¹ | ----R² | Salt data |
|---|---|---|---|---|---|
| 79 | B1 | 1 | 2-OMe-benzyl-O- | 2,4-difluorophenyl | |
| 80 | B1 | 1 | 3-MeO-benzyl-O- | 2,4-difluorophenyl | |
| 81 | B1 | 1 | 2-CF₃-benzyl-O- | 2,4-difluorophenyl | |

C. Analytical Part

LCMS

For (LC)MS-characterization of the compounds of the present invention, the following methods were used.

General Procedure 1

The HPLC measurement was performed using an Agilent 1100 module comprising a pump, a diode-array detector (DAD) (wavelength used 220 nm), and a column as specified in the respective methods below. Column flow was split to an Agilent MSD Series G1946C and G1956A. MS detector was configured with API-ES (atmospheric pressure electrospray ionization). Mass spectra were acquired in only positive ionization mode or in positive/negative modes by scanning from 100 to 1000 umas. The capillary needle voltage was 2500 V for positive ionization mode and 3000 V for negative ionization mode. Fragmentation voltage was 50 V. Drying gas temperature was maintained at 350° C. at a flow of 10 L/min.

Method A

In addition to general procedure 1: Reversed phase HPLC was carried out on a YMC-Pack ODS-AQ, 50×2.0 mm 5 μm column with a flow rate of 0.8 mL/min. A gradient with two mobile phases (A: water with 0.1% TFA; B: ACN with 0.05% TFA) was used in a total 7.5 minutes run. Typical injection volumes of 2 μL were used. Oven temperature was 50° C.

General Procedure 2

The HPLC (Ultra Performance Liquid Chromatography) measurement was performed using an Acquity HPLC (Waters) system comprising a sampler organizer, a binary pump with degasser, a four column's oven, a diode-array detector (DAD) and a column as specified in the respective methods below. Column flow was used without split to the MS detector. The MS detector was configured with an ESCI dual ionization source (electrospray combined with atmospheric pressure chemical ionization). Nitrogen was used as the nebulizer gas. Low-resolution mass spectra (single quadrupole, SQD detector) were acquired in positive/negative ionization modes by scanning from 100 to 1000 in 0.1 seconds using an inter-channel delay of 0.08 seconds. The capillary needle voltage was 3 kV. The cone voltage was 25V for positive ionization mode and 30V for negative ionization mode. The source temperature was maintained at 140° C.

Method B

In addition to the general procedure 2: Reversed phase HPLC was carried out on a BEH-C18 column (1.7 μm, 2.1× 50 mm) from Waters, with a flow rate of 1.0 mL/min, at 50° C. without split to the MS detector. A gradient with two mobile phases (A: 0.5 g/L ammonium acetate solution +5% ACN, B: ACN), were used in a total-5.0 minutes run. Injection volume 0.5 or 2.0 μL.

Melting Points

Values are either peak values or melt ranges, and are obtained with experimental uncertainties that are commonly associated with this analytical method.

DSC

For a number of compounds, melting points (m.p.) were determined with a Diamond DSC (PerkinElmer). Melting points were measured with a temperature gradient of 10° C./minute. Maximum temperature was 300° C. Values are peak values.

WRS-2A

For a number of compounds, melting points (m.p.) were determined with a WRS-2A melting point apparatus (Shanghai Precision and Scientific Instrument Co. Ltd.). Melting points were measured with a linear heating up rate of 0.2-5.0° C./minute. The reported values are melt ranges. The maximum temperature was 300° C. (indicated by WRS-2A in Table 2)

TABLE 2

Analytical data - $R_t$ means retention time (in minutes), [M + H]⁺ means the protonated mass of the compound, method refers to the method used for (LC)MS, n.d. means not determined.

| Comp. No. | $R_t$ | [M + H]⁺ | Method | Melting Point |
|---|---|---|---|---|
| 1 | 2.44 | 355 | B | 130° C. |
| 2 | 1.50 | 261 | B | 170.5° C. |
| 3 | 2.10 | 359 | B | n.d. |
| 4 | 1.90 | 319 | B | 82.6° C. |

TABLE 2-continued

Analytical data - $R_t$ means retention time (in minutes), [M + H]$^+$ means the protonated mass of the compound, method refers to the method used for (LC)MS, n.d. means not determined.

| Comp. No. | $R_t$ | [M + H]$^+$ | Method | Melting Point |
|---|---|---|---|---|
| 5 | 2.73 | 352 | B | n.d. |
| 6 | 4.62 | 373 | A | >280° C. |
| 7 | 4.97 | 362 | A | 87.2-87.8° C. (WRS-2A) |
| 8 | 1.76 | 275 | B | 141.5-142.4° C. (WRS-2A) |
| 9 | 6.57 | 355 | A | 163.3° C. |
| 10 | 1.62 | 275 | B | n.d. |
| 11 | 2.85 | 369 | B | 120.4° C. |
| 12 | 2.49 | 373 | B | 135° C. (WRS-2A) |
| 13 | 4.67 | 387 | A | 108-111.2° C. (WRS-2A) |
| 14 | 4.61 | 369 | A | 95.8-99.0° C. (WRS-2A) |
| 15 | 4.60 | 369 | A | 80.1-82.0° C. (WRS-2A) |
| 16 | 4.59 | 369 | A | 77.4-79.2° C. (WRS-2A) |
| 17 | 4.55 | 391 | A | 121.1-122.7° C. (WRS-2A) |
| 18 | 4.56 | 391 | A | 78.9-80.7° C. (WRS-2A) |
| 19 | 4.64 | 373 | A | 127.4-128.9° C. (WRS-2A) |
| 20 | 6.09 | 398 | A | 112.9° C. (WRS-2A) |
| 21 | 4.35 | 387 | A | 95.2-97.2° C. (WRS-2A) |
| 22 | 4.45 | 373 | A | 91.0-92.5° C. (WRS-2A) |
| 23 | 5.05 | 409 | A | 104.3-107.2° C. (WRS-2A) |
| 24 | 1.68 | 275 | B | 106.4° C. |
| 25 | 2.88 | 372 | B | 152.8° C. |
| 26 | 5.29 | 423 | A | 130.0-131.5° C. (WRS-2A) |
| 27 | 4.94 | 372 | A | 111.3-111.9° C. (WRS-2A) |
| 28 | 2.97 | 391 | B | n.d. |
| 29 | 5.63 | 373 | A | 268.9-284.1° C. (WRS-2A) |
| 30 | 5.26 | 423 | A | 108.2-108.9° C. (WRS-2A) |
| 31 | 4.58 | 373 | A | >280° C. |
| 32 | 6.05 | 391 | A | >280° C. |
| 33 | 4.69 | 363 | A | 98.4-99.6° C. (WRS-2A) |
| 34 | 4.83 | 363 | A | n.d. |
| 35 | 6.06 | 345 | A | n.d. |
| 36 | 5.60 | 385 | A | n.d. |
| 37 | 5.66 | 385 | A | 61.2-64.2° C. (WRS-2A) |
| 38 | 1.87 | 289 | B | 105.9° C. |
| 39 | 5.32 | 315 | A | 292.6-302.9° C. (WRS-2A) |
| 40 | 3.90 | 319 | A | 243.9-245.7° C. (WRS-2A) |
| 41 | 5.39 | 333 | A | 275.4-277.8° C. (WRS-2A) |
| 42 | 5.20 | 333 | A | 85.3-87.1° C. (WRS-2A) |
| 43 | 5.24 | 333 | A | 254.0-259.1° C. (WRS-2A) |
| 44 | 4.86 | 301 | A | 252.1-255.3° C. (WRS-2A) |
| 45 | 2.42 | 338 | B | 143.9° C. |
| 46 | 2.72 | 352 | B | 155.5° C. |
| 47 | 5.99 | 356 | A | 131.7-132.8° C. (WRS-2A) |
| 48 | 2.00 | 338 | B | n.d. |
| 49 | 2.09 | 338 | B | n.d. |
| 50 | 2.37 | 356 | B | n.d. |
| 51 | 2.71 | 352 | B | n.d. |
| 52 | 2.26 | 352 | B | n.d. |
| 53 | 5.93 | 374 | A | 185.8-186.8 V |
| 54 | 6.02 | 374 | A | 125.8-126.4° C. (WRS-2A) |
| 55 | 5.87 | 374 | A | 151.8-153.0° C. (WRS-2A) |
| 56 | 2.00 | 289 | B | 116° C. |
| 57 | 2.27 | 356 | B | 167.6° C. |
| 58 | 2.17 | 356 | B | n.d. |
| 59 | 5.92 | 391 | A | 100.1-105.2° C. (WRS-2A) |
| 60 | 2.52 | 389 | B | 186.9° C. |
| 61 | 4.96 | 319 | A | 235.8-240.2° C. (WRS-2A) |
| 62 | 4.97 | 319 | A | 126.3-130.8° C. (WRS-2A) |
| 63 | 5.42 | 303 | A | 104.1-106.0° C. (WRS-2A) |
| 64 | 5.57 | 321 | A | n.d. |
| 65 | n.d. | n.d. | n.d. | n.d. |
| 66 | n.d. | n.d. | n.d. | n.d. |
| 67 | n.d. | n.d. | n.d. | n.d. |
| 68 | n.d. | n.d. | n.d. | n.d. |
| 69 | n.d. | n.d. | n.d. | n.d. |
| 70 | n.d. | n.d. | n.d. | n.d. |
| 71 | n.d. | n.d. | n.d. | n.d. |
| 72 | n.d. | n.d. | n.d. | n.d. |
| 73 | 5.09 | 409 | A | 127.0-130.5° C. (WRS-2A) |
| 74 | 5.05 | 409 | A | 136.9-137.2° C. (WRS-2A) |
| 75 | 6.11 | 398 | A | 180.9-183.1° C. (WRS-2A) |
| 76 | 5.57 | 398 | A | 166.1-168.3° C. (WRS-2A) |
| 77 | 5.12 | 363 | A | n.d. |
| 78 | 5.25 | 441 | A | >280° C. (WRS-2A) |
| 79 | 4.03 | 403 | A | >280° C. (WRS-2A) |
| 80 | 4.95 | 403 | A | n.d. |
| 81 | 5.29 | 441 | A | >280° C. (WRS-2A) |

D. Pharmacological Examples

The compounds provided in the present invention are allosteric modulators of mGluR5, in particular, positive allosteric modulators of mGluR5. These compounds appear to potentiate glutamate responses by binding to an allosteric site other than the glutamate binding site. The response of mGluR5 to a concentration of glutamate is increased when compounds of Formula (I) are present. Compounds of Formula (I) are expected to have their effect substantially at mGluR5 by virtue of their ability to enhance the function of the receptor. The behaviour of positive allosteric modulators tested at mGluR5 using the intracellular $Ca^{2+}$ mobilization functional assay methods described below and which are suitable for the identification of such compounds.

Functional Assay 1

HEK-293 cells were stable transfected with human mGluR5a cDNA in expression vector pcDNA4/TO. For Assay 1, these human mGluR5 receptor over-expressing HEK-293 cells were grown at a density of 40,000 cells/well in PDL-coated 384-well plates. The following day, cells were preloaded with the calcium-sensing dye Fluo-4 AM and various concentrations of test compound were added in the absence of exogenous glutamate to test for direct agonist activity. Shortly (2.5 min) thereafter, an $EC_{20}$ equivalent of glutamate (~0.2 µM) was added. The fluorescence signal was monitored using a Hamamatsu Functional Drug Screening System (FDSS) fluorescence plate reader following the addition of compound alone (direct agonist response) and then the further addition of an $EC_{20}$ of glutamate (positive allosteric modulation response). The $pEC_{50}$ was defined as the negative log of the test compound concentration which produced an increase in the glutamate $EC_{20}$-mediated response that was 50% of maximum. Individual amplitudes were expressed as % effect by multiplying each amplitude by 100 and then dividing the product by the mean of the amplitudes derived from the glutamate $EC_{Max}$-treated wells. Emax values reported in this application are defined as the maximum % effect obtained in a concentration-response curve.

TABLE 3

Pharmacological data for compounds according to the invention in assay 1.

| Comp. No. | $pEC_{50}$ | $E_{max}$ (%) | $pEC_{50}$(*) |
|---|---|---|---|
| 1 | 5.89 | 64 | 6.07 |
| 8 | 5.87 | 88 | 5.96 |
| 12 | 5.71 | 71 | 6.26 |
| 14 | 5.29 | 88 | 5.35 |
| 15 | 5.43 | 67 | 5.59 |
| 16 | 5.27 | 88 | 5.44 |
| 17 | 6.16 | 82 | 6.13 |
| 18 | 6.21 | 76 | 6.29 |
| 23 | 6.02 | 54 | |
| 26 | 6.67 | 46 | |
| 27 | 6.96 | 57 | |

TABLE 3-continued

Pharmacological data for compounds according to the invention in assay 1.

| Comp. No. | $pEC_{50}$ | $E_{max}$ (%) | $pEC_{50}$(*) |
|---|---|---|---|
| 60 | <4.52 | 28 | |
| 65 | <4.52 | 25 | |
| 66 | <4.52 | 24 | |
| 69 | <4.52 | 15 | |
| 70 | <4.52 | 15 | |
| 71 | <4.52 | 8 | |
| 72 | <4.52 | 10 | |
| 74 | <4.52 | 32 | |
| 75 | <4.52 | 19 | |
| 76 | <4.52 | 19 | |
| 78 | <4.52 | 27 | |
| 79 | <4.52 | 21 | |
| 80 | <4.52 | 26 | |
| 81 | <4.52 | 25 | |

(*)means original value, which was updated as compound was further tested.

Functional Assay 2
Generation of Human mGluR5 Stable Cell Line

Human mGluR5a cDNA in pCMV6-XL6 mammalian expression plasmid was purchased from OriGene Technologies, Inc. (catalogue number SC326357) and subcloned into pcDNA3.1(−). Human embryonic kidney (HEK)293A cells were then transfected with human mGluR5a pcDNA3.1(−) using LipofectAmine-2000 (Invitrogen) and monoclones were selected and tested for functional response using a $Ca^{2+}$ mobilization assay. Monoclones were named for the species ("H" for human) plus the location on the plate (e.g. "10H").

Cell-Based Functional Assay

HEK cells transfected with the human mGluR5a receptor (H10H cell line) were plated at 15.000 cells/well in clear-bottomed poly-D-lysine-coated assay plates (BD Falcon) in glutamate-glutamine-free growth medium and incubated overnight at 37° C. and 5% CO2. The following day, the growth medium was removed and the cells were washed with assay buffer containing 1× Hank's balanced salt solution (Invitrogen, Carlsbad, Calif.), 20 mM HEPES, 2.5 mM probenecid, pH 7.4 and left with 20 µL of this reagent. Following this step, the cells were loaded with calcium indicator dye, fluo-4 AM, to a final concentration of 2 µM and incubated for 40-45 min at 37° C. The dye solution was removed and replaced with assay buffer. Cell plates were held for 10-15 min at room temperature and were then loaded into the Functional Drug Screening System 6000 (FDSS 6000, Hamamatsu, Japan).

After establishment of a fluorescence baseline for about 3 seconds, the compounds of the present invention were added to the cells, and the response in cells was measured. 2.3 minutes later an $EC_{20}$ concentration of the mGluR5 receptor agonist glutamate was added to the cells, and the response of the cells was measured for about 1.7 minutes. All test compounds were dissolved and diluted to a concentration of 10 mM in 100% DMSO and then serially diluted into assay buffer for a 2× stock solution in 0.6% DMSO; stock compounds were then added to the assay for a final DMSO concentration of 0.3% after the first addition to the assay well. Calcium fluorescence measures were recorded as fold over basal fluorescence; raw data was then normalized to the maximal response to glutamate. Potentiation of the agonist response of the mGluR5 receptor in the present invention was observed as an increase in response to submaximal concentrations of glutamate in the presence of compound compared to the response to glutamate in the absence of compound.

Data Analysis

The concentration-response curves of compounds of the present invention, obtained in the presence of $EC_{20}$ of mGluR5 receptor agonist glutamate to determine positive allosteric modulation, were generated using Microsoft Excel with IDBS XLfit add-ins. The raw data file containing all time points was used as the data source in the analysis template. This was saved by the FDSS as a tab-delimitted text file. Data were normalized using a static ratio function ($F/F_0$) for each measurement of the total 350 values per well divided by each well's initial value. Data was then reduced as to peak amplitudes (Max−Initial Min) using a time range that starts approximately 1 second after the glutamate $EC_{20}$ addition and continues for approximately 40 seconds. This is sufficient time to capture the peak amplitude of the cellular calcium response. Individual amplitudes were expressed as % effect by multiplying each amplitude by 100 and then dividing the product by the mean of the amplitudes derived from the glutamate $EC_{Max}$-treated wells. $pEC_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly. Individual values falling outside the 95% prediction limits of the curve fit were automatically excluded from the fit. A compound was designated as a positive allosteric modulator if the compound showed a concentration-dependent increase in the glutamate $EC_{20}$ addition. $E_{max}$ for compounds may be estimated using the resulting corresponding parameter value determined using the curve fit or by taking an average of the overall maximum response at a single concentration. These two methods are in good agreement for curves with a clear plateau at the high concentration range. For data that show an increase in the $EC_{20}$ response, but, do not hit a plateau, the average of the maximum response at a single concentration is preferred. For consistency purposes across the range of potencies observed, all Emax values reported in this application are calculated using the maximum average response at a single concentration. Table 4 below shows the pharmacological data obtained for a selected set of compounds.

TABLE 4

Pharmacological data for compounds according to the invention in assay 2.

| Comp. No. | $pEC_{50}$ | $E_{max}$ (%) |
|---|---|---|
| 1 | 6.51 | 57 |
| 2 | <5 | 84 |
| 3 | 5.64 | 78 |
| 4 | <5 | 69 |
| 5 | 5.92 | 84.5 |
| 6 | 6.34 | 75 |
| 8 | 5.85 | 77 |
| 11 | 6.67 | 81 |
| 12 | 6.74 | 67 |
| 13 | 5.73 | 48 |
| 14 | 5.65 | 52 |
| 15 | 6.04 | 59 |
| 16 | 5.91 | 56 |
| 17 | 6.53 | 61 |
| 18 | 6.37 | 72 |
| 19 | 6.67 | 38 |
| 20 | 6.80 | 25 |
| 21 | 6.48 | 54 |
| 22 | 6.43 | 45 |
| 24 | 5.46 | 45 |
| 25 | 6.76 | 63 |
| 29 | 7.01 | 81 |
| 31 | 6.55 | 71 |
| 32 | 6.65 | 81 |

TABLE 4-continued

Pharmacological data for compounds according to the invention in assay 2.

| Comp. No. | pEC$_{50}$ | E$_{max}$ (%) |
|---|---|---|
| 33 | <4.52 | 38 |
| 34 | 5.83 | 48 |
| 36 | 5.70 | 71 |
| 37 | 6.06 | 83 |
| 38 | 5.97 | 70 |
| 39 | 6.68 | 73 |
| 40 | 5.81 | 39 |
| 41 | 6.65 | 66 |
| 42 | 5.96 | 67 |
| 43 | 6.12 | 59 |
| 44 | 5.36 | 36 |
| 45 | 6.08 | 85 |
| 46 | 6.26 | 84 |
| 47 | 6.60 | 82 |
| 48 | 5.33 | 78 |
| 49 | 5.57 | 82 |
| 50 | 5.86 | 69 |
| 51 | 5.44 | 75 |
| 52 | 5.87 | 82 |
| 53 | 6.53 | 56 |
| 54 | 6.54 | 79 |
| 55 | 6.26 | 63 |
| 56 | 5.80 | 75 |
| 57 | 5.77 | 62 |
| 58 | 6.25 | 71 |
| 59 | 6.71 | 76 |
| 61 | <4.52 | 27 |
| 62 | <5 | 51 |
| 63 | 5.58 | 37.5 |
| 64 | <4.52 | 18 |
| 67 | <4.52 | 18 |
| 68 | <4.52 | 20 |
| 73 | <4.52 | 16 |

Functional Assay 3

Functional Assay 3 was performed under the same conditions as Functional Assay 2, except that clone H12H was used instead of clone H10H.

The clones that were used in the primary functional assay gave undiscernable differences in this assay.

TABLE 5

Pharmacological data for compounds according to the invention in assay 3.

| Comp. No. | pEC$_{50}$ | E$_{max}$ (%) |
|---|---|---|
| 7 | 5.85 | 57 |
| 9 | 6.95 | 79 |
| 28 | 7.07 | 63 |
| 30 | 6.03 | 58 |
| 35 | 6.10 | 60 |
| 77 | <4.52 | 21 |

Prospective In Vivo Effects

Generally clinically relevant antipsychotic agents (both typical and atypical) display efficacy in preclinical behavior challenge models. In vivo effects of the compounds described in the preceding examples are expected to be shown in various behavioural challenge models known to the skilled person, such as Amphetamine-, Phencyclidine (PCP)-induced hyperlocomotion in rodents and other models, such as NMDA receptor antagonists for example MK801.

In vivo effects of compounds having a structure represented by Formula (I) are expected to show activity in various behavioural challenge models known to the skilled person, such as Amphetamine-, Phencyclidine (PCP)-induced hyperlocomotion in rodents and other models, such as NMDA receptor antagonists for example MK801.

In Vivo Effects of 6,7-dihydro-5-methyl-2-(phenoxymethyl)-thiazolo[5,4-c]pyridin-4(5H)-one (compound 8) in the Rat Hyperlocomotion Assay

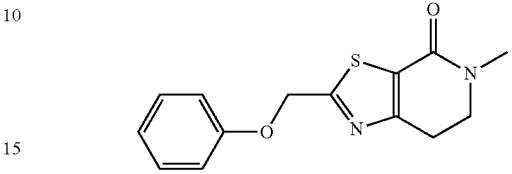

Locomotor activity was assessed as mean distance traveled (cm) in standard 16×16 photocell testing chambers measuring 43.2 cm (Length)×43.2 cm (Width)×30.5 cm (Height) (Med Associates, St. Albans, Vt.). Animals were habituated to individual activity chambers for at least 30 min prior to drug administration. Following administration of drug or vehicle, activity was recorded for a 90 minute time period. Data was expressed as the mean (±SEM) distance traveled recorded in 5 min intervals over the test period. The data was analyzed using repeated measures analysis of variance (ANOVA) followed by post-hoc testing using Dunnett's test, when appropriate. A difference was considered significant when p≤.05. Amphetamine sulfate was obtained from Sigma (Cat#A5880-1G; St. Louis, Mo.) and 10 mg was dissolved in 10 ml of water. Test compound 6,7-dihydro-5-methyl-2-(phenoxymethyl)-thiazolo[5,4-c]pyridin-4(5H)-one (compound 8) was formulated in a volume of 10 ml with an amount of drug appropriate to the dosage indicated. The appropriate amount of compound was mixed into a 20% 2-hydroxypropyl-β-cyclodextrin solution. The solution was formulated so that animals were injected with a volume equal to about 10× body weight. The mixture was then ultrahomogenized on ice for 2-3 minutes using the Dismembrator. Then the pH was checked using 0-14 EMD strips and adjusted to a pH of 6-7 if necessary. The mixture was then vortexed and stored in a warm sonication bath until time to be injected. Animals were administered samples of the following: (a) Amphetamine sulfate, 1 mg/kg, administered subcutaneously; (b) Compound 8, dose as indicated for FIG. 1 in Table 6 below, was administered by oral gavage; and (c) vehicle, pH 7, administered subcutaneously and intraperitoneally.

The study was carried out using male Sprague-Dawley rats weighing 225 g-275 g, between 2-3 months old (Harlan, Inc., Indianapolis, Ind.). They were kept in the animal care facility certified by the American Association for the Accreditation of Laboratory Animal Care (AALAC) under a 12-hour light/dark cycle (lights on: 6 a.m.; lights off: 6 p.m.) and had free access to food and water. The experimental protocols performed during the light cycle were approved by the Institutional Animals Care and Use Committee of Vanderbilt University and conformed to the guidelines established by the National Research Council Guide for the Care and Use of Laboratory Animals.

The animals were habituated in Smart Open Field locomotor activity test chambers (Hamilton-Kinder, San Diego, Calif.) with 16×16 photobeams to automatically record locomotor activity for 30 min and then dosed with vehicle or test compound. The rats were then placed into cages. At 60 min, all rats were injected subcutaneously with 1 mg/kg amphetamine or vehicle and then monitored for an additional 60 min.

Animals are monitored for a total of 120 minutes. Data are expressed as changes in ambulation defined as total number of beam breaks per 5 min periods.

The data for the dose-response studies were analyzed by a between-group analysis of variance. If there was a main effect of dose, then each dose group was compared with the vehicle amphetamine group. The calculations were performed using JMP IN 8 (SAS Institute, Cary, N.C.) statistical software and graphed using SigmaPlot9 (Saugua, Mass.). Results for reversal of amphetamine-induced hyperlocomotion by compound 8 is shown in FIG. 1. The line symbols and corresponding experimental conditions are shown below in Table 6. The table below uses the following abbreviations: (a) compound 8 (6,7-dihydro-5-methyl-2-(phenoxymethyl)-thiazolo[5,4-c]pyridin-4(5H)-one); (b) subcutaneous administration of compound is indicated by "sc"; (c) oral gavage administration is indicated by "po"; and (d) amphetamine sulfate is indicated as "amph". In the table, the vehicle for compound 8 is 20% wt/v β-CD and the vehicle for amphetamine is sterile water.

TABLE 6

| Line Symbol | Compound 8/Vehicle (as indicated; compound 8 dose in mg/kg) | Amph/Vehicle (as indicated; amph dose in mg/kg) |
| --- | --- | --- |
| ● | Vehicle, po | Amph, 1 mg/kg, sc |
| ○ | Compound 8, 3.0 mg/kg, po | Amph, 1 mg/kg, sc |
| ▼ | Compound 8, 10.0 mg/kg, po | Amph, 1 mg/kg, sc |
| △ | Compound 8, 30.0 mg/kg, po | Amph, 1 mg/kg, sc |
| ■ | Compound 8, 56.6 mg/kg, po | Amph, 1 mg/kg, sc |
| □ | Vehicle, po | Vehicle, sc |

E. Prophetic Composition Examples

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

| 1. Tablets | |
| --- | --- |
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

| 4. Ointment | |
| --- | --- |
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula (I)

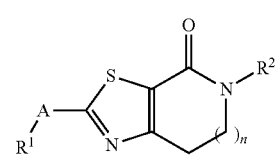

or a stereoisomeric form thereof,
wherein
n is 1;
A is selected from the group consisting of —CH$_2$O— and —O—CH$_2$—;
R$^1$ is selected from the group consisting of phenyl and phenyl substituted with 1, 2 or 3 substituents each independently selected from the group consisting of C$_{1-6}$alkyl, trifluoromethyl, cyano and halo; and
R$^2$ is selected from the group consisting of hydrogen; C$_{1-8}$alkyl; (C$_{1-6}$alkyloxy)C$_{1-3}$alkyl; C$_{3-8}$cycloalkyl; (C$_{3-8}$cycloalkyl)C$_{1-3}$alkyl; phenyl; phenyl substituted with 1, 2 or 3 substituents each independently selected from the group consisting of C$_{1-6}$alkyl, C$_{1-3}$alkyloxy, halo and C$_{1-3}$alkyl substituted with 1, 2 or 3 independently selected halo substituents; (phenyl)C$_{1-3}$alkyl; (phenyl)C$_{1-3}$alkyl wherein the phenyl part is substituted with 1, 2 or 3 independently selected halo substituents; pyridinyl; pyridinyl substituted with 1 or 2 substituents each independently selected from the group consisting of C$_{1-6}$alkyl, C$_{1-3}$alkyloxy, halo and C$_{1-3}$alkyl substituted with 1, 2 or 3 independently selected halo substituents; and (tetrahydro-2H-pyranyl)-methyl;
or a pharmaceutically acceptable salt thereof.

2. A compound of formula (I) according to claim 1, wherein
A is selected from the group consisting of —CH$_2$O— and —O—CH$_2$—;
R$^1$ is selected from the group consisting of phenyl; phenyl substituted with 1, 2 or 3 substituents each independently selected from the group consisting of C$_{1-3}$alkyl and fluoro; and 3-cyanophenyl; and
R$^2$ is selected from the group consisting of hydrogen; C$_{1-6}$alkyl; (C$_{1-6}$alkyloxy)C$_{1-3}$alkyl; C$_{3-8}$cycloalkyl; (C$_{3-8}$cycloalkyl)C$_{1-3}$alkyl; phenyl; phenyl substituted with 1, 2 or 3 substituents each independently selected from the group consisting of C$_{1-3}$alkyl, C$_{1-3}$alkyloxy, halo and C$_{1-3}$alkyl substituted with 1, 2 or 3 independently selected halo substituents; (phenyl)C$_{1-3}$alkyl; (phenyl)

C₁₋₃alkyl wherein the phenyl part is substituted with 1, 2 or 3 independently selected halo substituents; pyridinyl; pyridinyl substituted with 1 or 2 substituents each independently selected from the group consisting of C₁₋₃alkyl, C₁₋₃alkyloxy, halo and C₁₋₃alkyl substituted with 1, 2 or 3 independently selected halo substituents; and (tetrahydro-2H-pyranyl)-methyl;

or a pharmaceutically acceptable salt thereof.

3. The compound according to claim 1, wherein

A is —CH₂O—;

R¹ is selected from the group consisting of phenyl and phenyl substituted with 1, 2 or 3 substituents each independently selected from the group consisting of C₁₋₃alkyl and fluoro; and 3-cyanophenyl; and R² is selected from the group consisting of hydrogen; methyl; ethyl; 1,2,2-trimethyl-propyl; (C₁₋₆alkyloxy)C₁₋₃alkyl; C₃₋₈cycloalkyl; (C₃₋₈cycloalkyl)C₁₋₃alkyl; phenyl; phenyl substituted with 1, 2 or 3 substituents each independently selected from the group consisting of C₁₋₃alkyl, C₁₋₃alkyloxy, halo and C₁₋₃alkyl substituted with 1, 2 or 3 independently selected halo substituents; (phenyl)C₁₋₃alkyl; (phenyl)C₁₋₃alkyl wherein the phenyl part is substituted with 1, 2 or 3 independently selected halo substituents; pyridinyl; pyridinyl substituted with 1 or 2 substituents each independently selected from the group consisting of C₁₋₃alkyl, C₁₋₃alkyloxy, halo and C₁₋₃alkyl substituted with 1, 2 or 3 independently selected halo substituents; and (tetrahydro-2H-pyranyl)-methyl;

or a pharmaceutically acceptable salt thereof.

4. The compound according to claim 1, wherein

A is —CH2O—;

R¹ is selected from the group consisting of phenyl and phenyl substituted with 1 or 2 substituents each independently selected from the group consisting of C₁₋₃alkyl and fluoro; and R² is selected from the group consisting of hydrogen; methyl; ethyl; 1,2,2-trimethyl-propyl; (C₁₋₆alkyloxy)C₁₋₃alkyl; (C₃₋₈cycloalkyl)C₁₋₃alkyl; phenyl; phenyl substituted with 1 or 2 substituents each independently selected from the group consisting of C₁₋₃alkyl, C₁₋₃alkyloxy, halo and C₁₋₃alkyl substituted with 1, 2 or 3 independently selected halo substituents; (phenyl)C₁₋₃alkyl;

(phenyl)C₁₋₃alkyl wherein the phenyl part is substituted with 1 or 2 independently selected halo substituents; pyridinyl; pyridinyl substituted with 1 or 2 substituents each independently selected from the group consisting of C₁₋₃alkyl, C₁₋₃alkyloxy, halo and C₁₋₃alkyl substituted with 1, 2 or 3 independently selected halo substituents; and (tetrahydro-2H-pyranyl)-methyl;

or a pharmaceutically acceptable salt thereof.

5. The compound according to claim 1, wherein

A is —O—CH₂—;

R¹ is selected from the group consisting of phenyl; phenyl substituted with 1, 2 or 3 substituents each independently selected from the group consisting of C₁₋₃alkyl and fluoro; and 3-cyanophenyl; and R² is selected from the group consisting of C₁₋₃alkyl; (C₁₋₆alkyloxy)C₁₋₃alkyl; C₃₋₈cycloalkyl; (C₃₋₈cycloalkyl)C₁₋₃alkyl; phenyl; phenyl substituted with 1, 2 or 3 substituents each independently selected from the group consisting of C₁₋₃alkyl, C₁₋₃alkyloxy, halo and C₁₋₃alkyl substituted with 1, 2 or 3 fluoro substituents; (phenyl)C₁₋₃alkyl; (phenyl)C₁₋₃alkyl wherein the phenyl part is substituted with 1, 2 or 3 independently selected halo substituents; pyridinyl; pyridinyl substituted with 1 or 2 substituents each independently selected from the group consisting of C₁₋₃alkyl, C₁₋₃alkyloxy, halo and C₁₋₃alkyl substituted with 1, 2 or 3 fluoro substituents; and (tetrahydro-2H-pyranyl)-methyl;

or a pharmaceutically acceptable salt thereof.

6. A compound according to claim 1, selected from the group consisting of 5-(4-fluorophenyl)-6,7-dihydro-2-(phenylmethoxy)-thiazolo[5,4-c]pyridin-4(5H)-one, 6,7-dihydro-2-(phenoxymethyl)-thiazolo[5,4-c]pyridin-4(5H)-one, 6,7-dihydro-2-(phenoxymethyl)-5-[(tetrahydro-2H-pyran-4-yl)methyl]-thiazolo[5,4-c]pyridin-4(5H)-one, 6,7-dihydro-5-(2-methoxyethyl)-2-(phenoxymethyl)-thiazolo[5,4-c]pyridin-4(5H)-one, 6,7-dihydro-5-(5-methyl-2-pyridinyl)-2-(phenoxymethyl)-thiazolo[5,4-c]pyridin-4(5H)-one, 2-[(4-fluorophenoxy)methyl]-5-(4-fluorophenyl)-6,7-dihydro-thiazolo[5,4-c]pyridin-4(5H)-one, 2-[(3-fluorophenoxy)methyl]-6,7-dihydro-5-[(1R)-1,2,2-trimethylpropyl]-thiazolo[5,4-c]pyridin-4(5H)-one, 6,7-dihydro-5-methyl-2-(phenoxymethyl)-thiazolo[5,4-c]pyridin-4(5H)-one, 5-(4-fluorophenyl)-6,7-dihydro-2-(phenoxymethyl)-thiazolo[5,4-c]pyridin-4(5H)-one, 5-(2,4-difluorophenyl)-6,7-dihydro-2-(phenylmethoxy)-thiazolo[5,4-c]pyridin-4(5H)-one, 5-[(2,4-difluorophenyl)methyl]-6,7-dihydro-2-(phenylmethoxy)-thiazolo[5,4-c]pyridin-4(5H)-one, 5-[(4-fluorophenyl)methyl]-6,7-dihydro-2-(phenylmethoxy)-thiazolo[5,4-c]pyridin-4(5H)-one, 5-[(3-fluorophenyl)methyl]-6,7-dihydro-2-(phenylmethoxy)-thiazolo[5,4-c]pyridin-4(5H)-one, 5-[(2-fluorophenyl)methyl]-6,7-dihydro-2-(phenylmethoxy)-thiazolo[5,4-c]pyridin-4(5H)-one, 5-(2,4-difluorophenyl)-2-[(3-fluorophenyl)methoxy]-6,7-dihydro-thiazolo[5,4-c]pyridin-4(5H)-one, 5-(2,4-difluorophenyl)-2-[(2-fluorophenyl)methoxy]-6,7-dihydro-thiazolo[5,4-c]pyridin-4(5H)-one, 5-(4-fluorophenyl)-2-[(3-fluorophenyl)methoxy]-6,7-dihydro-thiazolo[5,4-c]pyridin-4(5H)-one, 3-[[[5-(2,4-difluorophenyl)-4,5,6,7-tetrahydro-4-oxothiazolo[5,4-c]pyridin-2-yl]oxy]methyl]-benzonitrile, 5-(2,4-difluorophenyl)-6,7-dihydro-2-[(3-methylphenyl)methoxy]-thiazolo[5,4-c]pyridin-4(5H)-one, 5-(4-fluorophenyl)-2-[(2-fluorophenyl)methoxy]-6,7-dihydro-thiazolo[5,4-c]pyridin-4(5H)-one, 5-(2,4-difluorophenyl)-2-[(2,4-difluorophenyl)methoxy]-6,7-dihydro-thiazolo[5,4-c]pyridin-4(5H)-one, 6,7-dihydro-5-methyl-2-(phenylmethoxy)-thiazolo[5,4-c]pyridin-4(5H)-one, 2-[(3-fluorophenoxy)methyl]-5-(4-fluorophenyl)-6,7-dihydro-thiazolo[5,4-c]pyridin-4(5H)-one, 2-[(3-fluorophenyl)methoxy]-6,7-dihydro-5-[4-(trifluoromethyl)phenyl]-thiazolo[5,4-c]pyridin-4(5H)-one, 5-(3-fluorophenyl)-2-[(3-fluorophenyl)methoxy]-6,7-dihydro-thiazolo[5,4-c]pyridin-4(5H)-one, 5-(2,4-difluorophenyl)-2-[(3-fluorophenoxy)methyl]-6,7-dihydro-thiazolo[5,4-c]pyridin-4(5H)-one, 5-(2,4-difluorophenyl)-6,7-dihydro-2-(phenoxymethyl)-thiazolo[5,4-c]pyridin-4(5H)-one, 2-[(3-fluorophenyl)methoxy]-6,7-dihydro-5-[3-(trifluoromethyl)phenyl]-thiazolo[5,4-c]pyridin-4(5H)-one, 2-[(2-fluorophenoxy)methyl]-5-(4-fluorophenyl)-6,7-dihydro-thiazolo[5,4-c]pyridin-4(5H)-one, 5-(2,4-difluorophenyl)-2-[(4-fluorophenoxy)methyl]-6,7-dihydro-thiazolo[5,4-c]pyridin-4(5H)-one, 2-[(2-fluorophenoxy)methyl]-6,7-dihydro-5-[(1R)-1,2,2-trimethylpropyl]-thiazolo[5,4-c]pyridin-4(5H)-one,
2-[(4-fluorophenoxy)methyl]-6,7-dihydro-5-[(1R)-1,2,2-trimethylpropyl]-thiazolo[5,4-c]pyridin-4(5H)-one,
6,7-dihydro-2-(phenoxymethyl)-5-[(1R)-1,2,2-trimethylpropyl]-thiazolo[5,4-c]pyridin-4(5H)-one,
2-[(2-fluorophenoxy)methyl]-6,7-dihydro-5-(2-methoxyphenyl)-thiazolo[5,4-c]pyridin-4(5H)-one,
2-[(3-fluorophenoxy)methyl]-6,7-dihydro-5-(2-methoxyphenyl)-thiazolo[5,4-c]pyridin-4(5H)-one,
5,6,7,8-tetrahydro-5-methyl-2-(phenoxymethyl)-4H-thiazolo[5,4-c]azepin-4-one,
5-(cyclopropylmethyl)-6,7-dihydro-2-(phenoxymethyl)-thiazolo[5,4-c]pyridin-4(5H)-one,
5-cyclopropyl-2-[(3-fluorophenoxy)methyl]-6,7-dihydro-thiazolo[5,4-c]pyridin-4(5H)-one,
5-(cyclopropylmethyl)-2-[(3-fluorophenoxy)methyl]-6,7-dihydro-thiazolo[5,4-c]pyridin-4(5H)-one,
5-(cyclopropylmethyl)-2-[(2-fluorophenoxy)methyl]-6,7-dihydro-thiazolo[5,4-c]pyridin-4(5H)-one,
5-(cyclopropylmethyl)-2-[(4-fluorophenoxy)methyl]-6,7-dihydro-thiazolo[5,4-c]pyridin-4(5H)-one,
5-cyclopropyl-6,7-dihydro-2-(phenoxymethyl)-thiazolo[5,4-c]pyridin-4(5H)-one,
6,7-dihydro-2-(phenoxymethyl)-5-(2-pyridinyl)-thiazolo[5,4-c]pyridin-4(5H)-one,
6,7-dihydro-5-(6-methyl-2-pyridinyl)-2-(phenoxymethyl)-thiazolo[5,4-c]pyridin-4(5H)-one,
5-(5-fluoro-2-pyridinyl)-6,7-dihydro-2-(phenoxymethyl)-thiazolo[5,4-c]pyridin-4(5H)-one,
6,7-dihydro-2-(phenoxymethyl)-5-(3-pyridinyl)-thiazolo[5,4-c]pyridin-4(5H)-one,
6,7-dihydro-2-(phenoxymethyl)-5-(4-pyridinyl)-thiazolo[5,4-c]pyridin-4(5H)-one,
5-(3-fluoro-2-pyridinyl)-6,7-dihydro-2-(phenoxymethyl)-thiazolo[5,4-c]pyridin-4(5H)-one,
6,7-dihydro-5-(4-methyl-2-pyridinyl)-2-(phenoxymethyl)-thiazolo[5,4-c]pyridin-4(5H)-one,
6,7-dihydro-5-(3-methyl-2-pyridinyl)-2-(phenoxymethyl)-thiazolo[5,4-c]pyridin-4(5H)-one,
2-[(4-fluorophenoxy)methyl]-5-(5-fluoro-2-pyridinyl)-6,7-dihydro-thiazolo[5,4-c]pyridin-4(5H)-one,
2-[(3-fluorophenoxy)methyl]-5-(5-fluoro-2-pyridinyl)-6,7-dihydro-thiazolo[5,4-c]pyridin-4(5H)-one,
2-[(2-fluorophenoxy)methyl]-5-(5-fluoro-2-pyridinyl)-6,7-dihydro-thiazolo[5,4-c]pyridin-4(5H)-one,
5-ethyl-6,7-dihydro-2-(phenoxymethyl)-thiazolo[5,4-c]pyridin-4(5H)-one,
5-(5-fluoro-3-pyridinyl)-6,7-dihydro-2-(phenoxymethyl)-thiazolo[5,4-c]pyridin-4(5H)-one,
5-(3-fluoro-4-pyridinyl)-6,7-dihydro-2-(phenoxymethyl)-thiazolo[5,4-c]pyridin-4(5H)-one,
5-(2,4-difluorophenyl)-2-[(2-fluorophenoxy)methyl]-6,7-dihydro-thiazolo[5,4-c]pyridin-4(5H)-one,
2-[(4-chlorophenoxy)methyl]-5-(4-fluorophenyl)-6,7-dihydro-thiazolo[5,4-c]pyridin-4(5H)-one,
5-cyclopropyl-2-[(2-fluorophenoxy)methyl]-6,7-dihydro-thiazolo[5,4-c]pyridin-4(5H)-one,
5-cyclopropyl-2-[(4-fluorophenoxy)methyl]-6,7-dihydro-thiazolo[5,4-c]pyridin-4(5H)-one,
6,7-dihydro-5-(1-methylethyl)-2-(phenoxymethyl)-thiazolo[5,4-c]pyridin-4(5H)-one,
2-[(3-fluorophenoxy)methyl]-6,7-dihydro-5-(1-methylethyl)-thiazolo[5,4-c]pyridin-4(5H)-one,
6,7-dihydro-2-(phenylmethoxy)-thiazolo[5,4-c]pyridin-4(5H)-one,
2-fluoro-5-[[(4,5,6,7-tetrahydro-4-oxothiazolo[5,4-c]pyridin-2-yl)oxy]methyl]-benzonitrile,
6,7-dihydro-2-[(2-methylphenyl)methoxy]-thiazolo[5,4-c]pyridin-4(5H)-one,
6,7-dihydro-2-[(3-methylphenyl)methoxy]-thiazolo[5,4-c]pyridin-4(5H)-one,
2-[(2-fluorophenyl)methoxy]-6,7-dihydro-thiazolo[5,4-c]pyridin-4(5H)-one,
2-[(2-fluorophenyl)methoxy]-6,7-dihydro-thiazolo[5,4-c]pyridin-4(5H)-one trifluoroacetate,
2-[(3-fluorophenyl)methoxy]-6,7-dihydro-thiazolo[5,4-c]pyridin-4(5H)-one,
2-[(3-fluorophenyl)methoxy]-6,7-dihydro-thiazolo[5,4-c]pyridin-4(5H)-one trifluoroacetate,
2-[(4-fluorophenyl)methoxy]-6,7-dihydro-thiazolo[5,4-c]pyridin-4(5H)-one,
2-[(4-fluorophenyl)methoxy]-6,7-dihydro-thiazolo[5,4-c]pyridin-4(5H)-one trifluoroacetate,
6,7-dihydro-2-[(4-methylphenyl)methoxy]-thiazolo[5,4-c]pyridin-4(5H)-one,
5-(2,4-difluorophenyl)-2-[(3,5-difluorophenyl)methoxy]-6,7-dihydro-thiazolo[5,4-c]pyridin-4(5H)-one,
5-(2,4-difluorophenyl)-2-[(3,4-difluorophenyl)methoxy]-6,7-dihydro-thiazolo[5,4-c]pyridin-4(5H)-one,
4-[[[5-(2,4-difluorophenyl)-4,5,6,7-tetrahydro-4-oxothiazolo[5,4-c]pyridin-2-yl]oxy]methyl]-benzonitrile,
2-[[[5-(2,4-difluorophenyl)-4,5,6,7-tetrahydro-4-oxothiazolo[5,4-c]pyridin-2-yl]oxy]methyl]-benzonitrile,
2-[(3-fluorophenyl)methoxy]-6,7-dihydro-5-[(1R)-1,2,2-trimethylpropyl]-thiazolo[5,4-c]pyridin-4(5H)-one,
5-(2,4-difluorophenyl)-6,7-dihydro-2-[[4-(trifluoromethyl)phenyl]methoxy]-thiazolo[5,4-c]pyridin-4(5H)-one,
5-(2,4-difluorophenyl)-6,7-dihydro-2-[(2-methoxyphenyl)methoxy]-thiazolo[5,4-c]pyridin-4(5H)-one,
5-(2,4-difluorophenyl)-6,7-dihydro-2-[(3-methoxyphenyl)methoxy]-thiazolo[5,4-c]pyridin-4(5H)-one, and
5-(2,4-difluorophenyl)-6,7-dihydro-2-[[2-(trifluoromethyl)phenyl]methoxy]-thiazolo[5,4-c]pyridin-4(5H)-one,
and the stereoisomeric forms, the pharmaceutically acceptable salts thereof.

7. A pharmaceutical composition comprising a therapeutically effective amount of a compound as defined in claim 1 and a pharmaceutically acceptable carrier.

* * * * *